(12) United States Patent
Breslin et al.

(10) Patent No.: US 9,090,907 B2
(45) Date of Patent: Jul. 28, 2015

(54) MODIFIED INSM1-PROMOTER FOR NEUROENDOCRINE TUMOR THERAPY AND DIAGNOSTICS

(75) Inventors: Mary B. Breslin, Metairie, LA (US); Michael S. Lan, Metairie, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 64 days.

(21) Appl. No.: 13/505,823

(22) PCT Filed: Nov. 8, 2010

(86) PCT No.: PCT/US2010/055844
§ 371 (c)(1),
(2), (4) Date: Aug. 16, 2012

(87) PCT Pub. No.: WO2011/071632
PCT Pub. Date: Jun. 16, 2011

(65) Prior Publication Data
US 2012/0316225 A1    Dec. 13, 2012

Related U.S. Application Data

(60) Provisional application No. 61/259,311, filed on Nov. 9, 2009.

(51) Int. Cl.
| | |
|---|---|
| *A61K 48/00* | (2006.01) |
| *C12Q 1/66* | (2006.01) |
| *C12N 15/00* | (2006.01) |
| *A01N 63/00* | (2006.01) |
| *C12N 15/86* | (2006.01) |
| *C07K 14/005* | (2006.01) |
| *C12N 15/85* | (2006.01) |

(52) U.S. Cl.
CPC ............ *C12N 15/86* (2013.01); *C07K 14/005* (2013.01); *C12N 15/85* (2013.01); *C07K 2319/55* (2013.01); *C07K 2319/61* (2013.01); *C12N 2710/10343* (2013.01); *C12N 2710/16622* (2013.01); *C12N 2710/16634* (2013.01); *C12N 2830/008* (2013.01); *C12N 2830/32* (2013.01); *C12N 2830/40* (2013.01)

(58) Field of Classification Search
None
See application file for complete search history.

(56) References Cited

U.S. PATENT DOCUMENTS

| 6,893,867 B1 | 5/2005 | Webster ............... 435/320.1 |
|---|---|---|
| 2005/0037445 A1 | 2/2005 | Poulsen ................. 435/7.23 |

FOREIGN PATENT DOCUMENTS

WO    WO 2008 / 039937    4/2008

OTHER PUBLICATIONS

Pedersen et al., 2006, Cancer Gene Therapy 13:375-384.*
Bessis et al 1997, PNAS. USA 94:5906-5911.*
Wang et al Jun. 2009, J. Biotechnology 142:193-199.*
Bell, A. C. et al., "The Protein CTCF is Required for the Enhancer Blocking Activity of Vertebrate Insulators," Cell, vol. 98, pp. 387-396 (1999).
Breslin, M. B. et al., "NeuroD1/E47 Regulates the E-box Element of a Novel Zinc Finger Transcription Factor, IA-1, in Developing Nervous System,", J. Biol. Chem, vol. 278, pp. 38991-38997 (2003).
Chung, J. H. et al., "A 5' Element of the Chicken β-Globin Domain Serves as an Insulator in Human Erythroid Cells and Protects against Position Effect in *Drosophila*," Cell, vol. 74, pp. 505-514 (1993).
Chung, J. H. et al., "Characterization of the Chicken β-globin insulator," Proc. Natl. Acad. Sci. U. S. A., vol. 94, pp. 575-580 (1997).
Duggan, A. et al., "Transient Expression of the Conserved Zinc Finger Gene INSM1 in Progenitors and Nascent Neurons Throughout Embryonic and Adult Neurogenesis," J. Comp Neurol., vol. 507, pp. 1497-1520 (2008).
Goto, Y. et al., "A Novel Human Insulinoma-associated cDNA, IA-1, Encodes a Protein with 'Zinc-finger' DNA-binding Motifs," J. Biol. Chem., vol. 267, No. 21, pp. 15252-15257 (1992).
Guglielmi, L. et al., "Insulators to Improve Expression of a 3-IgH LCR-driver Reporter Gene in Transgenic Mouse Models," Biochem. Biophys. Res. Commun, vol. 307, pp. 466-471 (2003).
Hanawa, H. et al., "Optimized Lentiviral Vector Design Improves Titer and Transgene Expression of Vectors Containing the Chicken β-Globin Locus HS4 Insulator Element," Mol. Ther., vol. 17, No. 4, pp. 667-674 (2009).
Kuruppu, D. et al., "HSV-1 Viral Oncolysis and Molecular Imaging with PET," Curr. Cancer Drug Targets., vol. 7, No. 2, pp. 175-180 (2007).

(Continued)

*Primary Examiner* — Christopher M Babic
*Assistant Examiner* — Kelaginamane T Hiriyanna
(74) *Attorney, Agent, or Firm* — John H. Runnels; Bonnie J. Davis

(57) ABSTRACT

A modification of the existing INSM1 promoter region has been discovered that incorporated DNA elements that silence expression of neuronal genes in non-neuronal cells and that has increased the effectiveness and safety of using the INSM1 promoter for tumor treatment. One modification was addition of one or two tandem copies of neuronal restrictive silencer elements (NRSEs) derived either from the mouse nicotinic acetylcholine receptor (nAChR) or the rat superior cervical ganglion 10 (SCG10) promoters. These NRSEs were placed in the expression construct either directly upstream or downstream of the INSM1 promoter sequence. The most effective expression construct was the nAChR NRSE element positioned downstream of the INSM1 promoter. This expression construct increased the tissue specificity of the INSM1 promoter without a significant decrease in its activity. In addition, the modified INSM1 promoter was placed into a viral vector, adenovirus 5. Constructs with an insulator element, the chicken HS4 β-globin insulator element, with the INSM1 promoter was shown to decrease the interference of the viral genome on its expression. Constructs have been made that do not decrease the INSM1 promoter activity but significantly augment the tumor specificity of the promoter. Linking the construct to a reporter gene allowed for detection of the placement of the viral vector, and this detection can be used for diagnosing or locating neuroendocrine tumors.

12 Claims, 12 Drawing Sheets

(56) References Cited

OTHER PUBLICATIONS

Lan, M. S. et al., "IA-1, a New Marker for Neuroendocrine Differentiation in Human Lung Cancer Cell Lines," Cancer Res., vol. 53, pp. 4169-4171 (1993).

Lan, M. S. et al., "Structure, expression, and biological function of INSM1 transcription factor in neuroendocrine differentiation," FASEB J., vol. 23, pp. 2024-2033 (2009).

Lanigan, T. M. et al., "Binding of Upstream Stimulatory Factor and a Cell-specific Activator to the Calcitonin/Calcitonin Gene-related Peptide Enhancer," J. Biol. Chem., vol. 272, No. 29, pp. 18316-18324 (1997).

Li, Q. et al., "Molecular Characterization of the Promoter Region of a Neuroendocrine Tumor Marker, IA-1," Biochem. Biophys. Res. Commun, vol. 236, pp. 776-781 (1997).

Mellitzer, G. et al., "IA1 is NGN3-dependent and essential for differentiation of the endocrine pancreas," EMBO J., vol. 25, pp. 1344-1352 (2006).

Mutskov, V. J. et al., "The barrier function of an insulator couples high histone acetylation levels with specific protection of promoter DNA from methylation," Genes Dev., vol. 16, pp. 1540-1554 (2002).

Namikawa, K. et al., "A Newly Modified SCG10 Promoter and Cre/loxP-mediated Gene Amplification System Achieve Highly Specific Neuronal Expression in Animal Brains," Gene Therapy, vol. 13, pp. 1244-1250 (2006).

Pedersen, N. et al., "The insulinoma-associated 1: a novel promoter for targeted cancer gene therapy for small-cell lung cancer," Cancer Gene Ther., vol. 13, pp. 375-384 (2006).

Ren, X-W et al., "A tumor-specific conditionally replicative adenovirus vector expressing TRAIL for gene therapy of hepatocellular carcinoma," Cancer Gene Ther., vol. 13, pp. 159-168 (2006).

Symes, A. J. et al., "Loss of transcriptional repression contributes to the ectopic expression of the calcitonin/α-CGRP gene in a human lung carcinoma cell line," FEBS, vol. 306, No. 2,3, pp. 229-233 (1992).

Taniwaki, M. et al., "Gene expression profiles of small-cell lung cancers: Molecular signatures of lung cancer," Int. J. Oncol., vol. 29, pp. 567-575 (2006).

Tverberg, L. A. et al., "Regulation of the Calcitonin/Calcitonin Gene-related Peptide Gene by Cell-specific Synergy between Helix-Loop-Helix and Octamer-binding Transcription Factors," J. Biol. Chem., vol. 268, No. 21, pp. 15965-15973 (1993).

Viney, T. J. et al., "Regulation of the Cell-specific Calcitonin/Calcitonin Gene-related Peptide Enhancer by USF and the Foxa2 Forkhead Protein," J. Biol. Chem., vol. 279, No. 48, pp. 49948-49955 (2004).

Wada, C. et al., "Developmentally regulated expression of the calcitonin gene related peptide (CGRP) in rat lung endocrine cells," Virchows Arch. B Cell Pathol. Incl. Mol. Pathol., vol. 55, pp. 217-223 (1988).

Wang, H.-W. et al., "INSM1 Promoter-Driven Adenoviral Herpes Simplex Virus Thymidine Kinase Cancer Gene Therapy for the Treatment of Primitive Neuroectodermal Tumors," Human Gene Ther, vol. 20, pp. 1308-1318 (2009).

Xie, J. et al., "The Zinc-Finger Transcription Factor INSM1 is Expressed during Embryo Development and Interacts with the Cbl-Associated Protein," Genomics, vol. 80, pp. 54-61 (2002).

Yamamoto, M. et al., "Transcription Initiation Activity of Adenovirus Left-End Sequence in Adenovirus Vectors with E1Deleted," J. Virol., vol. 77, No. 2, pp. 1633-1637 (2003).

Yusufzai, T. M. et al., "The 5'HS4 chicken β-globin insulator is a CTCF-dependent nuclear matrix-associated element," Proc. Natl. Acad. Sci. U. S. A, vol. 101, No. 23, pp. 8620-8624 (2004).

* cited by examiner

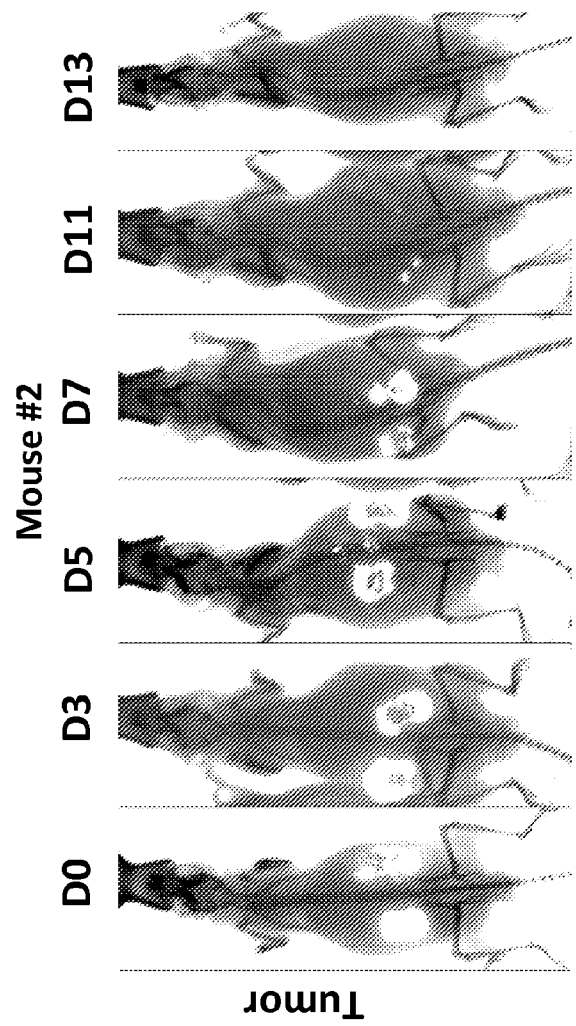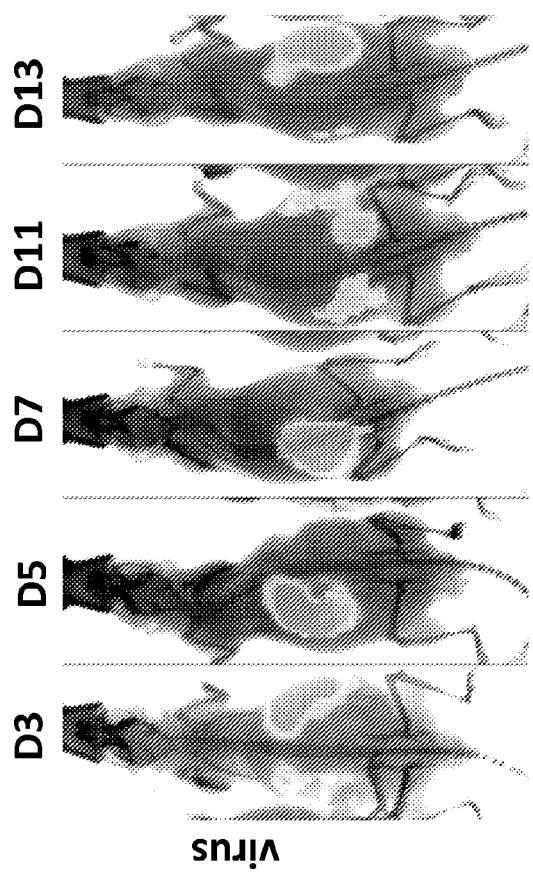

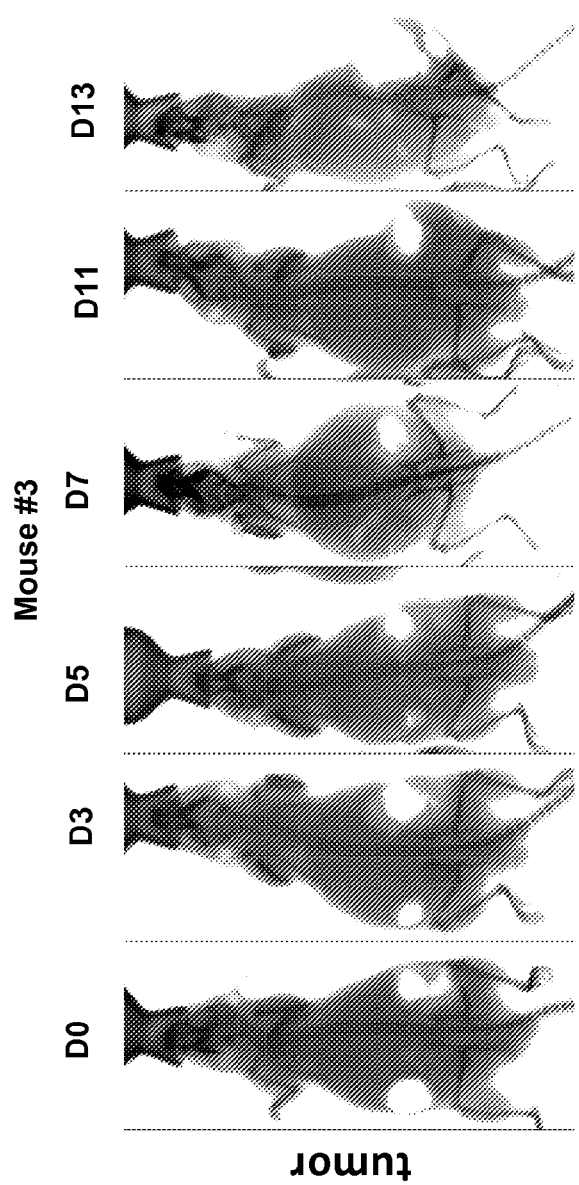
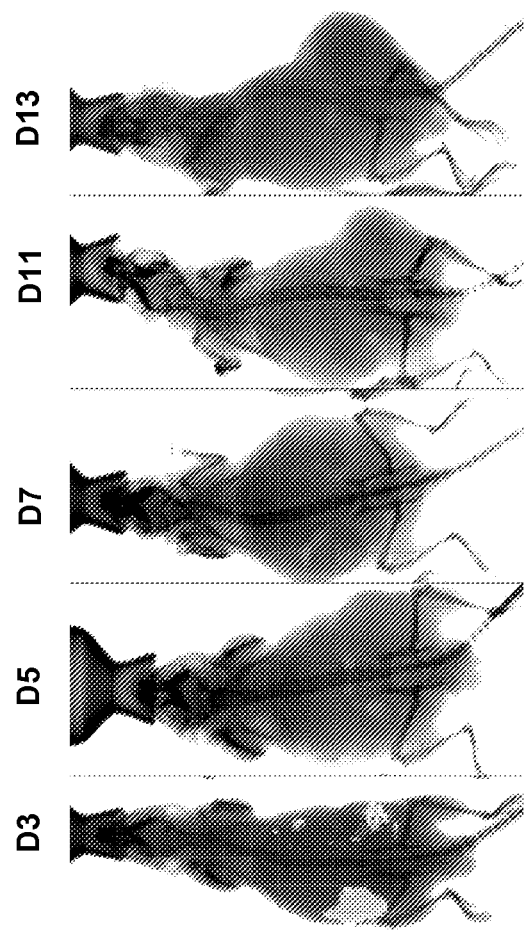

SEQUENCE LISTING

```
<160> NUMBER OF SEQ ID NOS: 7

<210> SEQ ID NO 1
<211> LENGTH: 60
<212> TYPE: DNA
<213> ORGANISM: Artificial sequence
<220> FEATURE:
<223> OTHER INFORMATION: Synthetic primer

<400> SEQUENCE: 1
cagatctttc agcaccacgg agagtgcctt cagcaccacg gagagtgcca agcttggtac    60

<210> SEQ ID NO 2
<211> LENGTH: 63
<212> TYPE: DNA
<213> ORGANISM: Artificial sequence
<220> FEATURE:
<223> OTHER INFORMATION: Synthetic primer

<400> SEQUENCE: 2
caagcttaga ggcactctcc gtggtgctga aggcactctc cgtggtgctg aaagatctgg    60
tac                                                                   63

<210> SEQ ID NO 3
<211> LENGTH: 62
<212> TYPE: DNA
<213> ORGANISM: Artificial sequence
<220> FEATURE:
<223> OTHER INFORMATION: Synthetic primer

<400> SEQUENCE: 3
cagatctttc agcaccacgg acagcgctct tcagcaccac ggacagcgct caagcttggt    60
ac                                                                    62

<210> SEQ ID NO 4
<211> LENGTH: 62
<212> TYPE: DNA
<213> ORGANISM: Artificial sequence
```

```
<220> FEATURE:
<223> OTHER INFORMATION: Synthetic primer

<400> SEQUENCE: 4
caagcttgag cgctgtccgt ggtgctgaag agcgctgtcc gtggtgctga aagatctggt      60
ac                                                                    62

<210> SEQ ID NO 5
<211> LENGTH: 36
<212> TYPE: DNA
<213> ORGANISM: Artificial sequence
<220> FEATURE:
<223> OTHER INFORMATION: Synthetic primer

<400> SEQUENCE: 5
cagatctggc agctgtgcaa atcctaagct tggtac                               36

<210> SEQ ID NO 6
<211> LENGTH: 36
<212> TYPE: DNA
<213> ORGANISM: Artificial sequence
<220> FEATURE:
<223> OTHER INFORMATION: Synthetic primer

<400> SEQUENCE: 6
caagcttagg atttgcacag ctgccagatc tggtac                               36

<210> SEQ ID NO 7
<211> LENGTH: 26
<212> TYPE: DNA
<213> ORGANISM: Artificial sequence
<220> FEATURE:
<223> OTHER INFORMATION: Synthetic primer

<400> SEQUENCE: 7 ctcccccgt ataaaggag cggctg                                            26
```

MODIFIED INSM1-PROMOTER FOR NEUROENDOCRINE TUMOR THERAPY AND DIAGNOSTICS

This is the United States national stage of international application PCT/US2010/055844, international filing date Nov. 8, 2010, which claims the benefit of the filing date of provisional U.S. application Ser. No. 61/259,311, filed Nov. 9, 2009, under 35 U.S.C. §119(e).

TECHNICAL FIELD

This invention is for the treatment and/or diagnosis of human neuroendocrine tumors using an expression construct comprising the nucleic acid sequence from the human insulinoma-associated 1 (INSM1) promoter (nucleotides −1661 to +40 bp or portion thereof) and one or more elements selected from neuron restrictive silencer elements and insulator elements. The construct can contain a suicide or toxin gene for treatment of tumors and/or a reporter gene for visualization or detection. In addition, the construct may be linked directly with a reporter gene for diagnosis of neuroendocrine tumors.

BACKGROUND ART

Insulinoma-associated 1 (INSM1) is a transcriptional repressor protein that is required for the development of the endocrine pancreas, adrenal gland, basal neuronal progenitor cells in the neocortex, and the monoaminergic neurons in the hindbrain (1). INSM1 expression is restricted to early fetal development in neuronal and endocrine tissues (2-6). One striking feature of the INSM1 mRNA is despite its absence in normal adult tissues, it is strongly expressed in tumors of neuroendocrine origin such as small cell lung carcinoma (SCLC), medullablastoma, neuroblastoma, medullary thyroid carcinoma, insulinoma, retinoblastoma, pheochromocytoma, and pituitary tumors (7-9). Using a transgenic animal model and in vitro reporter gene assays, the spatial and temporal expression of INSM1 has been demonstrated to be regulated by the 5' 1.7 kilobase pair promoter region (10;11). The 1.7 kbp promoter region has been linked to a suicide gene for delivery into tumor cells. The ability of the INSM1 promoter to drive expression of the herpes simplex virus thymidine kinase gene selectively has been tested in small cell lung cancer (SCLC) cells and in pediatric brain tumors (12;13; see also, U.S. Patent Application Publication No. 2005/0037445). Adenoviral vectors are one of the most widely exploited viral delivery systems for gene therapy due to their ability to infect a wide range of host cells and the minimal risk associated with the use of a non-replicating form of the virus. The adenovirus genome is easily manipulated and with the deletion of the E1 and E3 genes allows for the incorporation of up to 7.5 kilobase pairs of exogenous sequence. However, one major drawback of adenovirus is host mediated immunity to the virus. In addition, due to the high liver transduction efficiency following intravenous delivery of adenovirus, the liver is most susceptible to toxic side effects.

DISCLOSURE OF THE INVENTION

We have discovered that modification of the existing INSM1 promoter region to incorporate DNA elements that have silenced expression of neuronal genes in non-neuronal cells has increased the effectiveness and safety of using the INSM1 promoter for tumor treatment. To increase the safety of the transcriptionally regulated suicide gene therapy, various DNA elements were included in the 1.7 kilobase pair INSM1 promoter to test for reduction in expression in unwanted tissues. The first modification was addition of two tandem copies of neuronal restrictive silencer elements (NRSEs) derived either from the mouse nicotinic acetylcholine receptor (nAChR) or the rat superior cervical ganglion 10 (SCG10) promoters. These NRSEs were placed in the construct either directly upstream or downstream of the INSM1 promoter sequence. The most effective construct was the nAChR NRSE element positioned downstream of the INSM1 promoter. This construct increased the tissue specificity of the INSM1 promoter without a significant decrease in its activity. We have successfully tested the INSM1 promoter linked to a toxin for tumor therapy. We placed the constructs into a viral vector, using adenovirus 5. We also tested constructs with an insulator element with the INSM1 promoter to decrease the interference of the viral genome on its expression. A construct using the chicken HS4 β-globin insulator element was shown to work as expected. Linking the construct to a reporter gene allows for detection of the placement of the viral vector, and can be used for diagnosing neuroendocrine tumors. We have discovered constructs that do not decrease the INSM1 promoter activity but significantly augment the tumor specificity of the promoter. We have shown that these constructs when placed in a viral vector can be used for treatment and diagnosing of neuroendocrine tumors.

BRIEF DESCRIPTION OF THE DRAWINGS

FIG. 5A illustrates the in vivo imaging on days 0, 3, 5, 7, 11 and 13 to monitor the progression of INSM1 promoter viral gene therapy and effect on tumor size in Mouse #2 injected initially with $1 \times 10^7$ NCI-H1155 red fluorescent SCLC cells to visualize a tumor mass, and then given a single intratumoral injection of $1 \times 10^9$ ifu (infection units) of the Ad-INSM1p-HSV-tkIRES-Luc2 virus. The location and size of the tumor mass is visualized suing the red fluorescence of the SCLC cells.

FIG. 5B illustrates the in vivo imaging on days 0, 3, 5, 7, 11 and 13 to monitor the progression of INSM1 promoter viral gene therapy in Mouse #2 injected initially with 1×10⁷ NCI-H1155 red fluorescent SCLC cells, and then given a single intratumoral injection of 1×10⁹ ifu of the Ad-INSM1p-HSV-tkIRES-Luc2 virus. Prior to imaging in FIG. 5B, the mice were given a 100 μl intraperitoneal injection of 15 mg/ml D-luciferin to detect luciferase activity.

FIG. 6A illustrates the in vivo imaging on days 0, 3, 5, 7, 11 and 13 to monitor the progression of INSM1 promoter viral gene therapy and effect on tumor size in Mouse #3 injected initially with 1×10⁷ NCI-H1155 red fluorescent SCLC cells to visualize a tumor mass, and then given a single intratumoral injection of 1×10⁹ ifu of the Ad-INSM1p-HSV-tkl-RES-Luc2 virus. The location and size of the tumor mass is visualized suing the red fluorescence of the SCLC cells.

FIG. 6B illustrates the in vivo imaging on days 0, 3, 5, 7, 11 and 13 to monitor the progression of INSM1 promoter viral gene therapy in Mouse #3 injected initially with 1×10⁷ NCI-H1155red fluorescent SCLC cells, and then given a single intratumoral injection of 1×10⁹ ifu of the Ad-INSM1p-HSV-tkIRES-Luc2 virus. Prior to imaging in FIG. 6B, the mice were given a 100 μl intraperitoneal injection of 15 mg/ml D-luciferin to detect luciferase activity.

MODES FOR CARRYING OUT THE INVENTION

Figure 1:
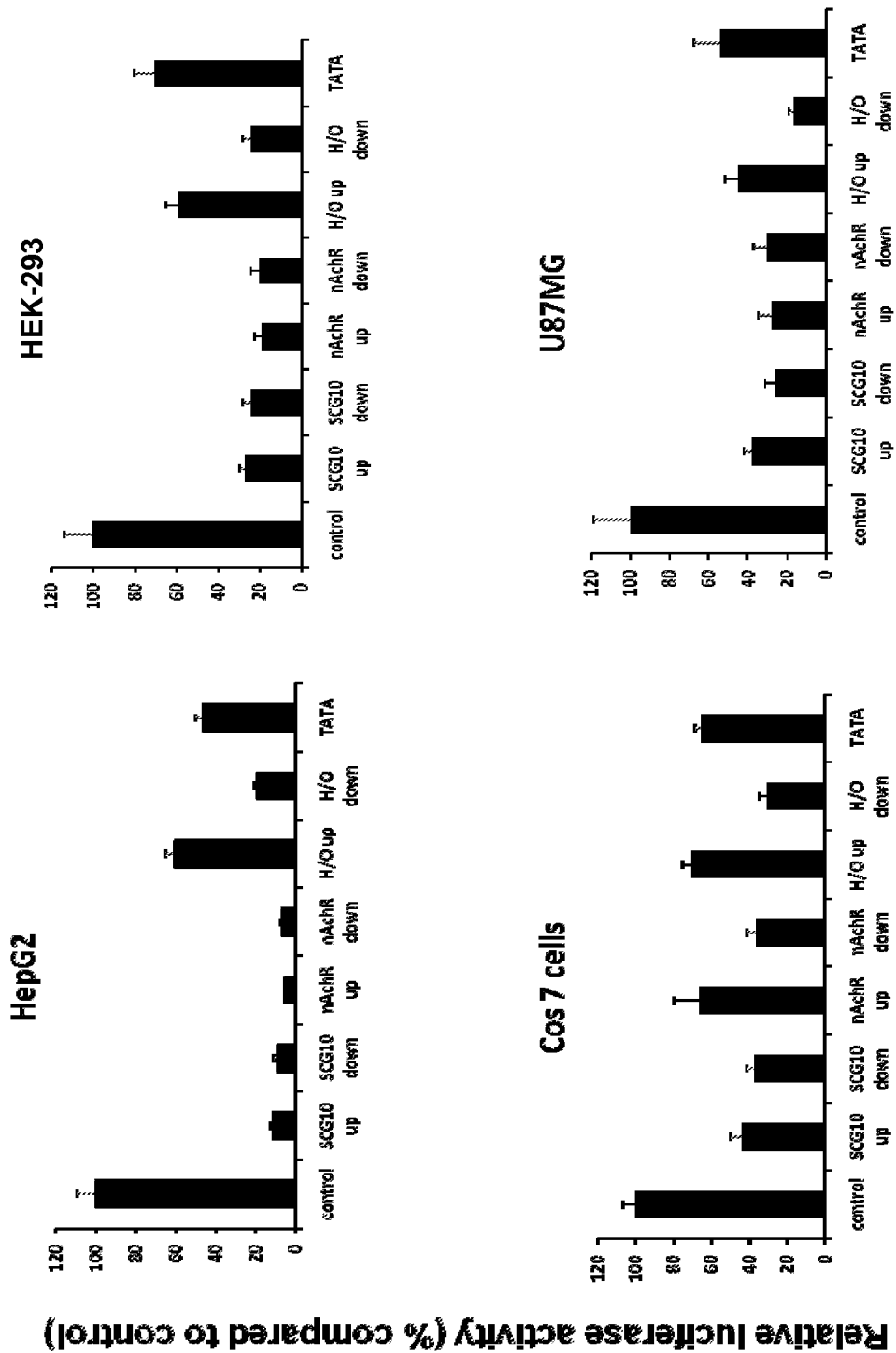
FIG. 1 illustrates the effect of modifications to the INSM1 promoter on the luciferase reporter gene activity at 24 hours post transfection as compared to the controls in non-neuronal human cells, i.e., in HepG2 (hepatocellular carcinoma), HEK-293 (embryonic kidney), Cos7* (African green monkey kidney), or U87MG (glioblastoma) cells. All transfections were performed in triplicate on at least three occasions.

We have modified the INSM1 promoter region to incorporate DNA elements that have silenced expression of neuronal genes in non-neuronal cells, and this modification has increased the effectiveness and safety of using the INSM1 suicide gene therapy for tumor treatment. To increase the safety of the transcriptionally regulated suicide gene therapy, various DNA elements were included in the 1.7 kilobase pair INSM1 promoter to test for reduction in expression in unwanted tissues. One of the modifications was addition of two tandem copies of neuronal restrictive silencer elements (NRSEs) derived either from the mouse nicotinic acetylcholine receptor (nAChR) or the rat superior cervical ganglion 10 (SCG10) promoters. These NRSEs were placed in the construct either directly upstream or downstream of the INSM1 promoter sequence. The most effective construct was the nAChR NRSE element positioned downstream of the INSM1 promoter. This construct increased the tissue specificity of the INSM1 promoter without a significant decrease in its activity. We have successfully tested the modified INSM1 promoter for suicide gene therapy by linking it to a toxin for tumor therapy, the herpes simplex virus-thymidine kinase gene. We placed the constructs into a viral vector, using adenovirus 5, for delivery directly to tumor cells or by injection intraperitoneally or intravenously. We also tested constructs with an insulator element with the INSM1 promoter to decrease the interference of the viral genome on its expression. A construct using the chicken HS4 β-globin insulator element was successfully tested. Linking the construct to a reporter gene allows for detection of the localization of the viral vector, and can be used for diagnosing neuroendocrine tumors. We have discovered constructs that do not decrease the INSM1 promoter activity but significantly augment the tumor specificity of the promoter. We have shown that these constructs when placed in a viral vector can be used for treatment and diagnosing of neuroendocrine tumors.

As used in the specification and in the claims, the term "construct" or "expression construct" refers to a functional DNA nucleotide sequence that is artificially constructed to transfer or express one or more genes of interest.

As used in the specification and in the claims, the term "neuronal restrictive silencer element" or "NRSE" is a DNA segment that is known to mediate transcriptional repression of many neuron-specific genes via the neuron-restrictive silencer factor (NRSF) or repressor element silencing transcription factor. The neuron-restrictive silencer element (NRSE) has been identified in several neuronal genes and confers neuron specificity by silencing transcription in non-neuronal cells. NRSE elements when bound by its cognate protein, the neuron restrictive silencing factor, NRSF, can strongly repress transcription in non-neuronal cells as well as allow transcription of the same gene in neuronal cells. Examples of neuronal restrictive silencer elements (NRSEs) include those derived either from the mouse nicotinic acetylcholine receptor (nAChR) or the rat superior cervical ganglion 10 (SCG10) promoters. Multiple neuronal genes have been shown to be repressed by NRSF protein via a NRSE element located in their promoter regions. Other neuronal genes repressed by NRSF in non-neuronal cells include protocadherin, tryptophan hydroxylase-2, mu opioid receptor, tyrosine hydroxylase, N-methyl-D-aspartate receptor 2B, proprotein convertase 2, glutamate receptor 2, GluR2, arginine vasopressin, brain-derived neutrophic factor, neural-specific type II sodium channel, and dopamine beta hydroxylase genes. (See also, U.S. Patent Application Publication No. 2006/0121013)

As used in the specification and in the claims, the term "insulator element" is a DNA segment that has the ability to protect genes from inappropriate signals originating from the surrounding environment by acting as a physical barrier or boundary. An insulator element blocks the interaction between a promoter and enhancers when it is inserted between them, or it confers expression of integrated foreign genes independent of their position in the chromatin. The 5' HS4 element, derived from the chicken β-globin locus (the first insulator identified in vertebrates), has been used with success to improve heterologous construct expression in transgenic animals. The chicken β⁻-globin HS4 insulator element has been shown to block the actions of enhancer elements in addition to functioning as a physical boundary that can prevent the spread of gene silencing (14-20). In this embodiment of the construct, the insulator element is used to prevent the adenoviral sequences from potentially interrupting the INSM1 promoter activity and to prevent the interference from the viral backbone with respect to the tissue selectivity of the promoter incorporated into the viral vectors.

As used in the specification and in the claims, the term "reporter gene" refers to a gene, usually a foreign or modified gene, that is added to a construct and is expressed due to the promoter in the construct and the expression allows easy identification of cells or tissues that have taken up the construct. Common reporter genes include the gene that encodes jellyfish green fluorescent protein, which causes cells that express it to glow green under UV light, and the firefly luciferase gene which causes light emission when its substrate luciferin is added. Reporter genes are often placed downstream of the promoter region and in the proximity of the gene of interest to ensure that they are expressed together and not separated by crossover events.

As used in the specification and in the claims, the term "toxin gene" refers to a gene that encodes a toxin that is capable of being readily produced either under the regulatory control of the INSM1 promoter. A "toxin" is a gene product(s) that causes or leads to the destruction or incapacitation of a cell. This definition is intended to include the induction of indigenous events leading to cell death, such as apoptosis or necrosis. A "toxin" may, for example, be a compound that induces conditional lethality, i.e., cell death requires both expression of a conditional toxin gene (for example, thymidine-kinase) and the exogenous administration of a compound (for example, ganciclovir or acyclovir) that together produce a lethal effect. Another example is the combination of the gene encoding cytosine deaminase and the pro-drug 5-fluorocytosine. For example, a suitable toxin may be one of the many toxic peptides known in the art. In addition, the toxin should be capable of killing tumor cells or, optionally, the toxin may also kill neighboring cells, a "bystander" effect, but it should not have substantial systemic effects. There are numerous toxins from plants, animals, and bacteria satisfying these criteria, including naturally occurring, modified and synthetic toxins. Examples of toxins include without limitation synthetic and natural lytic peptides, cholera toxin, diphtheria toxin, *Pseudomonas* toxin, ricin toxin, cecropins, defensins, sarcotoxins, melittins, and magainins. One suicide gene therapy uses the gene herpes simplex virus thymidine kinase and ganciclovir. The disadvantage to this system includes significant liver toxicity unless precaution is taken to decrease its expression in liver cells. (See also, discussion in PCT/US00/0633 published as WO005377; U.S. Pat. Nos. 5,789,542 and 6,566,334.)

As used in the Specification and in the Claims, the term "viral vector" refers to a virus that is competent to infect a mammalian host cell and can be used to deliver the construct to the target cells or tumor or to an animal systemically. One example of a viral vector is the first generation E1/E3 deleted non-replicating Ad5 vector, but other forms of viral delivery systems are known and could be used. One of the disadvantages of the non-replicating adenovirus is the lack of persistence in vivo and one embodiment could be the use of a conditionally replicating oncolytic adenovirus. Additional examples of viral delivery systems include viruses that would result in more permanent expression such as lentivirus or adeno-associated virus (AAV). The advantage to these two viral systems is that they can be manipulated to alter their tropism for different cell types making them a more flexible platform.

Neuroendocrine tumors that can be treated or diagnosed using the described construct include without limitation retinoblastoma, medullablastoma, neuroblastoma, small cell lung carcinoma, non-small cell carcinoma with neuroendocrine phenotype, carcinoid, insulinoma, pheochromocytoma, medullary thyroid carcinoma, pituitary tumors, prostate carcinoma, and retinoblastoma tumors.

Example 1

Materials and Methods

Modifications to the INSM1 Promoter Region.

To functionally test the effect of inclusion of various neuronal specific DNA elements to the INSM1 promoter activity, all the constructs were compared in the pGL3 or pGL4 luciferase reporter vector (Promega Corp., Madison, Wis.). The human INSM1 promoter developed by one of the inventors (Dr. M. S. Lan) from nucleotides −1661 to +40 bp was subcloned into the Sma I site of the pGL3 Basic vector. Proper orientation of the INSM1 promoter region was confirmed by restriction endonuclease digestion as described (13). The unmodified INSM1 promoter-luciferase construct was used as the control vector for all comparisons. To modify the promoter region, two tandem copies of the neuronal restrictive silencer element (NRSE) derived from either the superior cervical ganglion 10 (SCG10) or nicotinic acetylcholine receptor (nAchR) promoter regions were synthesized (Eurofins MWG Operon, Huntsville, Ala.) and cloned either upstream or downstream with respect to the INSM1 promoter transcription initiation site. All enzymes used for cloning, e.g., restriction enzymes, ligase, phosphatase, and kinase, were obtained from New England Biolabs (NEB) (Ipswitch, Mass.) unless otherwise noted. In addition, all chemicals were purchased from Sigma-Aldrich (St. Louis, Mo.) unless otherwise noted.

Briefly, the pGL3B-INSM1 promoter constructs were digested with either KpnI (upstream) or BglII (downstream) purified using a QiaQuik purification kit (Qiagen; Valencia, Calif.) followed by alkaline phosphatase treatment to prevent vector self-ligation. All synthetic oligonucleotides were commercially synthesized by Eurofins MWG Operon Inc. (Huntsville, Ala.), and included a Kpn I half-site and a BglII restriction site at both ends of the two tandem copies of the SCG10 or n(AchR) NRSE element. The oligonucleotide sequence for the SCG10 NRSE element was as follows: 5'-cagatct(TTCAGCACCACGGAGAGTGCC)(TTCAGCACCACGGAGAGTGCC)aagcttggtac-3' (SEQ ID NO:1) and the reverse complement 5'-caagcttaga (GGCACTCTCCGTGGTGCTGAA) (GGCACTCTCCGTGGTGCTGAA) agatctggtac-3' (SEQ ID NO:2). The oligonucleotides generated for the n(AchR) NRSE were the sense 5'-cagatct (TTCAGCACCACGGACAGCGCTC) (TTCAGCACCACGGACAGCGCTC)aagcttggtac-3'(SEQ ID NO:3) and reverse complement 5'-caagctt(GAGCGCTGTCCGTGGTGCTGAA)(GAGCGCTGTCCGTGGTGCTGAA)agatctggtac-3' (SEQ ID NO:4). The oligonucleotides were annealed by heating at 95° C. for 5 minutes and slow cooled at 1° C./minute in a PCR machine (iCycler; BioRad, Hercules, Calif.) to generate double strand products. The ends of the double strand 2×NRSE oligonucleotides were phosphorylated with $T_4$ polynucleotide kinase in the presence of ATP to facilitate ligation. The oligonucleotides were ligated at room temperature using $T_4$ DNA ligase (NEB) into the pGL3B-INSM1 promoter KpnI-treated vector to create the 2×NRSE up constructs. Alternatively, the double strand oligonucleotides were digested with BglII, purified by phenol/chloroform extraction followed by ethanol precipitation. The BglII digested oligonucleotides were ligated at room temperature with the pGL3B-INSM1 promoter BglII treated vector to generate the 2×NRSE down modified INSM1 promoter constructs.

The same procedure was performed to clone the H/O enhancer into the INSM1 promoter luciferase reporter constructs. The DNA element derived from the CT/CGRP gene known as the H/O enhancer was synthesized and included a KpnI and BglII sites in the linker region with 2 tandem repeats of the H/O enhancer sequence, sense oligonucleotides 5' cagatctGGCAGCTGTGCAAATCCTaagcttggtac 3' (SEQ ID NO:5) and reverse compliment primer 5' caagcttAGGATTTGCACAGCTGCCagatctggtac 3 (SEQ ID NO:6). Finally, the INSM1 promoter region (−34 to −27 bp) spanning the putative TATA-like element was mutated using the Quik Change II Site-Directed Mutagenesis Kit (Stratagene) with the oligonucleotides 5' CTCCCCCCGTATAAAAGGAGCGGCTG 3' (SEQ ID NO:7) and the reverse compliment to convert the sequence into a consensus TATA-binding site (TTAAAGG to TATAAAAG). The bold nucleotides are the position of the changes that were incorporated into the INSM1 promoter sequence.

Figure 9:
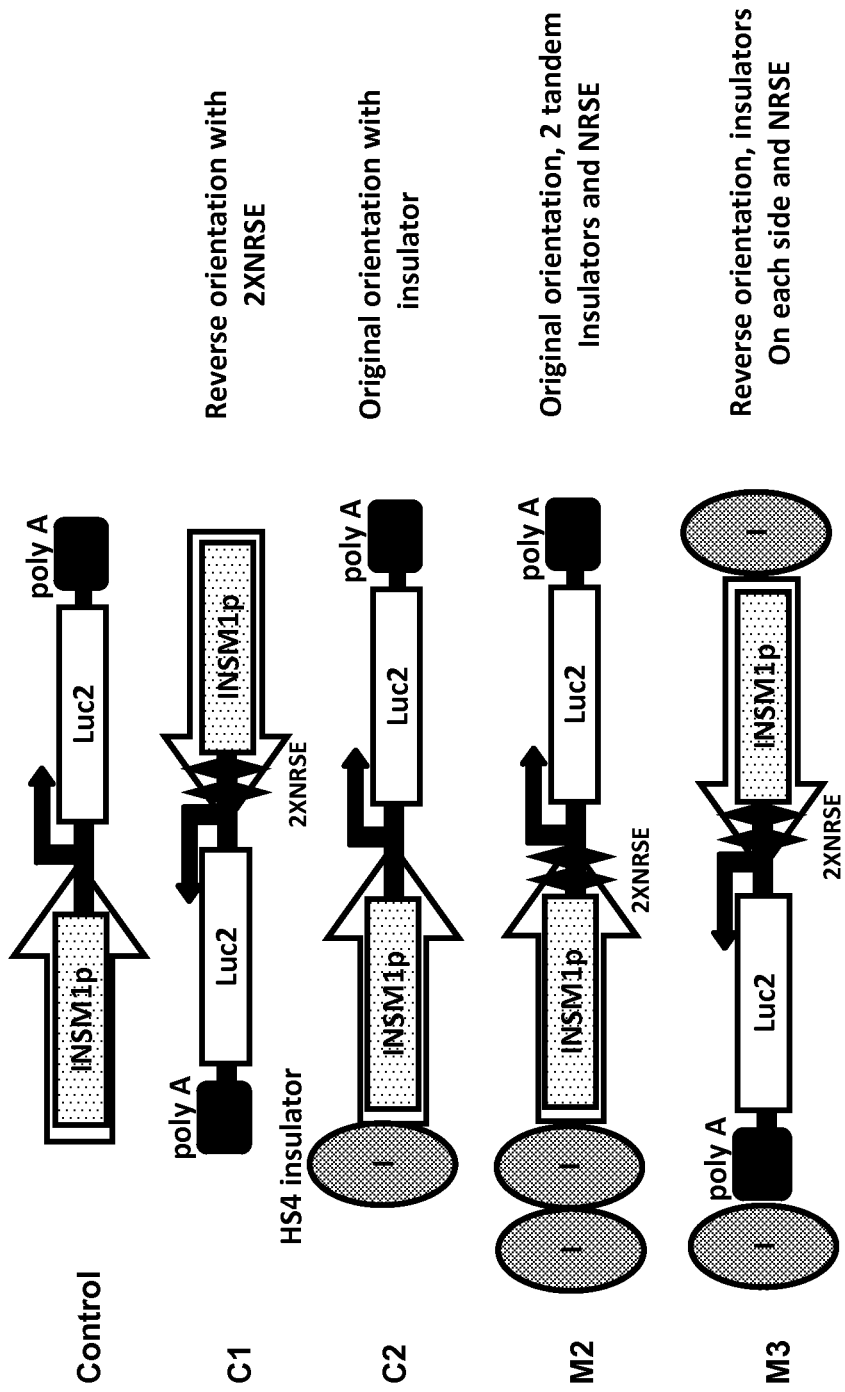
FIG. 9 is a schematic diagram of several new configurations of the INSM1 promoter luciferase constructs: C or control is the original configuration of the viral constructs; C1 is the whole transgene cloned in the opposite orientation with the addition of the 2×AchR NRSE elements; C2 is the original promoter construct with a HS4 chicken β-globin insulator; M2 contains two upstream copies of the HS4 chicken β-globin insulator and the 2×AchR NRSEs; and M3 contains the INSM1p 2×AchR NRSE cloned in the opposite orientation and flanked on both sides by the HS4 insulator elements.

Constructs incorporating either an insulator and/or NRSE element were generated to determine if they would enhance the specificity of the INSM1 promoter driven cancer gene therapy. The promoter constructs were generated in the pGL3 luciferase reporter gene vectors (Promega) and subsequently transferred into the adenoviral backbone. All restriction endonuclease enzymes used were from New England Biolabs (Ipswich, Mass.) unless otherwise noted. FIG. 9 is a schematic showing the four constructs created as described below. The pGL3 vector was digested with Sma I and treated with calf intestinal alkaline phosphatase (New England Biolabs, Ipswich, Mass.) to prevent self ligation of the vector and the −1661/+40 bp INSM1 promoter is cloned into the Sma I site of the pGL3 basic luciferase vector (Promega). The orientation was verified by restriction digest and DNA sequencing. The 2×nAChR NRSE element was cloned by digesting the pGL3 INSM1 promoter construct with Bgl II and inserting the 2×nAChR NRSE downstream of the INSM1 promoter (adjacent to the +40 bp region). Next, the luciferase gene was removed by Nco I/Sal I double digest and replaced with the luciferase 2 (Nco I/Sal I) gene from the pGL4 (Promega) vector creating the C1Luc2 construct (FIG. 9). One copy of the HS4 β-globin insulator element was digested with Kpn I from the pJC13-1 vector (obtained from Dr. Gary Felsenfeld, National Institutes of Health), and ligated upstream of the 5' end of the INSM1 promoter by digestion of the pGL3-INSM1 promoter-Luc2 vector with KpnI creating construct C2Luc2 (FIG. 9). Two copies of the insulator element were cloned into the Kpn I site of the pGL3 vector at the 5' end of the INSM1 promoter containing the 2×NRSE element and was designated the M2Luc2 construct. (See FIG. 9) The final construct generated contained the INSM1 promoter-2×NRSE element-Luc2 gene that is flanked on the 5' end of the INSM1 promoter with one copy of the HS4 insulator element at the Kpn I site as described above. A second copy of the HS4 insulator element was inserted into the Xba I site at the 3' end of the luciferase 2 gene by digestion with XbaI of the INSM1 luciferase vector and the HS4 insulator pNI vector (obtained from Dr. Gary Felsenfeld, National Institutes of Health) to create the M3Luc2 construct (FIG. 9). The only two constructs that lack the 2×NRSE modification are the original control INSM1pLuc2 and the C2Luc2 constructs. The modified DNA constructs were purified by CsCl gradient and quantitated using a GE nanovue spectrophotometer.

Transient Transfection for Reporter Gene Assays:

All human cells lines were obtained from American Type Culture Collection (ATCC) (Manassass, Va.) and were cultured in Royal Parks Memorial Institute (RPMI) 1640 or Dulbecco's modified eagle's media (DMEM) containing 10% fetal bovine serum (FBS) and 1% penicillin/streptomycin in a 37° C. incubator with 5% $CO_2$. All cell culture media was obtained from Mediatech (Manassass, Va.) unless otherwise noted. Twenty-four hours prior to transient transfection, the cells were seeded at 75,000 cells/well in a 24-well culture dish. Transient transfections included 400 ng pGL3B-INSM1p control or INSM1p-modified constructs and 100 ng TK-Renilla control plasmid (Promega, Madison, Wis.) for normalization of transfection efficiency. DNA was mixed at a ratio of 1:2 with TransFectin Lipid reagent (BioRad, Hercules, Calif.) in Gibco Optimem (Invitrogen, Carlsbad, Calif.) for 30 minutes prior to addition to the wells. All transfections were done in triplicate on at least three separate occasions to confirm the experimental results. Twenty four hours post transient transfection, the cells were collected, washed once in 1×PBS, and the cell pellet was resuspended in a final volume of 100 ∞l of PBS. Twenty-five microliters of the cell suspension was mixed one to one with Dual Glo luciferase reagent (Promega; Madison, Wis.) and incubated at room temperature for 10 minutes in a white 96-well plate. The luciferase activity was measured using a TopCount NXT microplate scintillation and luminescence reader (Packard Instrument Company, Meriden, Conn.). Twenty five microliters of Stop and Glo reagent (Promega, Madison, Wis.) was subsequently added to the wells and following an additional ten minute incubation the plate was re-read to detect Renilla luciferase activity for normalization of transfection efficiency. Data were graphed as the mean of the luciferase activity divided by the renilla activity, and were graphed relative to the controlINSM1pLuc2 constructs that are set to 100%.

Generation of Adenoviral Constructs and Viral Lysates.

In order to generate Ad5 virus for gene therapy studies, the INSM1 promoter Luc2 constructs were transferred into the pShuttle plasmid backbone (Stratagene; Agilent Technologies, Santa Clara, Calif.). The C1, C2, M2, and M3 Luciferase 2 constructs were digested with Cla I to remove the various HS4 insulator INSM1promoter 2×NRSE luciferase 2 expression cassette from the pGL3 vector backbone. The Cla I site was filled-in with Klenow (New England Biolabs) enzyme. The pShuttle vector was prepared by digestion with EcoRV and treated with calf intestinal alkaline phosphatase (New England Biolabs) to prevent self ligation of the vector backbone. Positive clones were verified by restriction digestion and DNA sequence analysis. To generate the equivalent HSV thymidine kinase containing constructs, the INSM1 promoter with the 2×NRSE element was removed from the pGL3 vector with Cla I/HindIII and the ends filled-in by Klenow (New England Biolabs). The pShuttle vector containing the HSVtk gene was prepared by digestion with EcoRV followed by calf intestinal alkaline phosphatase (CIP, NEB). Insulator elements were inserted into the Kpn I site or both the KpnI and Xba I sites of the pShuttle vector to generate C1TK, C2TK, M2TK, and M3TK constructs.

To generate adenovirus, the INSM1promLuc2 or INSM1promHSVtk pShuttle constructs were digested with Pme I and treated with calf intestinal alkaline phosphatase (New England Biolabs). The linearized pShuttle constructs were electroporated into BJ5183 Ad-1 electrocompetent E. coli cells (40 µl, Stratagene; Agilent Technologies, Santa Clara, Calif.) in a 0.2 cm cuvette with a BioRad electroporator with the settings 2.5 kV, 200 ohms, and 25 µF. The kanamycin resistant colonies were screened for the recombination between the pShuttle vector and Ad5 genome. Positive clones are transformed into XL-10 Gold chemically competent cells (Stratagene; Agilent Technologies, Santa Clara, Calif.) and DNA purified using a Qiagen Midi prep kit (Qiagen, Valencia, Calif.). Recombinant adenovirus DNA is linearized with Pac I and transfected into Ad-293 producer cells with Fugene6 lipid reagent 1:1 DNA lipid ratio (Roche Applied Science, Indianapolis, Ind.). Ten to 12 days following the initial transfection, the cells were collected and subjected to three rounds of freeze-thaw-lysis to release the viral particles. The viral supernatant was re-infected into Ad-293 cells (human embryonic kidney, Agilent Technologies, Santa Clara, Calif.) for at least two more rounds of amplification. The final round of amplification was done with 30-150 cm tissue culture dishes and the viral lysate was purified on a CsCl gradient. The viral supernatant was dialyzed to remove the CsCl before use. The final viral amplification was titered using the Adeno-X-Rapid Titer Kit (Clontech, Mountain View, Calif.) and stored at −70° C.

In Vitro Tests of Viral Efficacy and Specificity.

Experiments were conducted comparing the effectiveness of the AdRSV-β-galactosidase (negative control), Ad-RSV-HSVtk (positive control), Ad-INSM1prom-HSVtk (INSM1 control), Ad-INSM1prom-2×NRSE-HSVtk (C1Tk), Ad-HS4 insulator-INSM1prom-HSVtk (C2Tk), Ad-2× copies HS4 insulator-INSM1prom-2×NRSE-HSVtk (M2Tk), and Ad-HS4 insulator-INSM1prom-2×NRSE-HSVtk-H54 insulator (M3Tk). INSM1 positive NCI-H69 (ATCC HTB-119 human small cell lung cancer, (SCLC), NCI-H82 (ATCC HTB-175 human SCLC-variant), NCI-H1155 (ATCC CRL-5818, human non small cell lung cancer (NSCLC), SHP-77 (ATCC CRL-2195, human SCLC), NCI-H727 (ATCC CRL-5815, human lung carcinoid), Y79 (ATCC HTB-18, human retinoblastoma), WERI-Rb1 (ATCC HTB-169, human retinoblastoma), D283 Med (ATCC HTB-185, human medullablastoma), IMR-32 (ATCC CCL-127 human neuroblastoma), TT (ATCC CRL-1803 human medullary thyroid carcinoma), SK-N-BE(2) (ATCC CRL-2271, human neuroblastoma), and INSM1 negative U87MG (ATCC HTB-14, human glioblastoma), HepG2 (ATCC HB-8065, human hepatocellular carcinoma), HEK-293 (ATCC CRL-1573, human embryonic kidney), BEAS-2B (ATCC CRL-9609, human bronchial epithelial, and NL20 (ATCC CRL-2503, human bronchial epithelial) cells were purchased from ATCC and grown according to its recommendations. The cells were seeded at 20,000-40,000 cells per well in a 96 well dish. The cells are treated with 0, 50, 100, or 200 MOI (multiplicity of infection) of each Ad-HSVtk virus. Twenty-four hours post virus infection, the cells were treated with 100 µm ganciclovir (GCV) for five days and an MTS assay (Promega; Madison, Wis.) was performed to determine cell viability. Expression of HSV thymidine kinase protein in the INSM1 positive cell lines was verified by western blot analysis. INSM1 positive cell lines (H69, H1155, SHP-77, H727, Y79, WERI-Rb1, D283, IMR-32, TT, SK-N-BE(2)) were seeded in a 60 cm dish and infected with MOI 100 Ad-RSV-HSVtk, AdINSM1 control, AdINSM1 C1Tk, AdINSM1 C2Tk, AdINSM1M2Tk, and AdINSM1M3Tk. Forty eight hours later, the cells were collected and lysed in RIPA buffer (1% NP-40, 1% sodium deoxycholate, 0.1% SDS, 150 mm NaCl, 10 mm Tris-Cl pH 7.4) containing complete protease inhibitor cocktail (Roche Applied Science, Indianapolis, Ind.). The cells were sonicated and centrifuged to clear the lysate. The protein lysates were quantitated using a Pierce BCA protein assay kit (Thermo Fisher Scientific, Rockford, Ill.), and equal amounts of total protein were loaded in each well on a 12% SDS-PAGE gel. The gel was transferred to nitrocellulose membrane. The membrane was incubated with a 1:1000 dilution of rabbit anti-HSV thymidine kinase antibody (Dr. W. Summers, Yale University) in 5% nonfat milk/TBS, followed by incubation with a 1:10,000 dilution of goat anti-rabbit horse radish peroxidase (HRP) secondary antibody (BioRad, Hercules, Calif.). Finally, the membrane is incubated with ImmunStar HRP substrate (BioRad, Hercules, Calif.) and imaged using a Kodak Gel Logic 2200 imager (Carestream Health, Woodbridge, Conn.).

In Vivo Biodistribution Studies:

To verify specificity of the promoter constructs, 8 week male Athymic Ncr nu/nu (NCI, Fredrick, Md.) mice were injected with $1 \times 10^6$ H1155Cherry fluorescent tumor cells subcutaneously in the hind flank, and the tumor cells were allowed to grow for 7-10 days. The H1155 cherry fluorescent cells were generated by infection of H1155 cells with a lentivirus (pNL CMV-vectors, Jakob Reiser, Food and Drug Administration, Bethesda, Md.) that were engineered to express the cherry fluorescent gene (pmCherry vector, Clontech, MountainView, Calif.). A pure population of H1155 cherry cells was obtained by sorting on a fluorescence activated cell sorter (FACS) and expanding the fluorescent cells in culture. The mice were divided into groups of three mice, and were injected with $1 \times 10^9$ ifu adenovirus either via intratumoral or intravenous into the tail vein. Forty eight hours post virus injection, the mice were imaged on a Kodak In Vivo FX multispectral imager (Carestream Health, Woodbridge, Conn.). Prior to imaging, the animals were injected intraperitoneal with 100 µl 15 mg/ml D-luciferin. The animals were immobilized with isoflurane (2-4% by inhalation) for imaging using the program X-ray 2 minutes, luminescence 10 minute acquisition, and fluorescence 30 seconds acquisition. Following imaging, the animals were euthanized by $CO_2$ inhalation and the heart, lungs, liver, kidney, spleen, pancreas, and tumors were removed and frozen in 1-5 mls Glo-lysis buffer (Promega). The tissues were homogenized with a tissue homogenizer and centrifuged to clear the homogenate. Total tissue protein was determined by a Pierce BCA protein assay kit (Thermo Fisher Scientific, Rockford, Ill.) and 300 µg total protein per tissue was used to determine luciferase activity. The luciferase activity was measured using a Steady-Glo® Luciferase Assay Kit (Promega, Madison, Wis.).

In Vivo Tumor Efficacy:

Eight week old male Nu/Nu mice (NCI Fredrick, Fredrick, Md.) were injected with $1\times10^6$ H1155 Red tumor cells subcutaneously into the hind flanks and allowed to grow for 7-10 days. The tumors were injected with $1\times10^9$ ifu virus particles with both the Ad-INSM1p-HSVtk and Ad-INSM1pLuc2 containing constructs to simultaneously visualize the location/expression pattern of the virus and to determine the killing effect of the cancer gene therapy. The animals received daily intraperitoneal injections of ganciclovir (50 mg/kg body weight). Elimination of the tumor cells was measured manually by caliper and visually by injection of 100 µl 15 mg/ml D-luciferin followed immediately by image analysis with the Kodak In vivo FX multispectral imager as described above. The animal's tumors were followed for 2 weeks and the tumor growth or regression was measured every other day.

Reporter Gene Assay In Vitro Diagnostics:

Tumor biopsy will be weighed and placed into 96 well culture dishes. Tumors will be infected with $1\times10^8$ ifu adenovirus particles for 24 hours. Five µl 3 mg/ml D-luciferin will be added directly to the well, incubated at room temperature for 10 minutes and the firefly luciferase 2 activity measured on the TopCounter (Packard instruments). Alternatively, INSM1 promoter adenovirus constructs containing Metridia luciferase as the reporter gene will be used. Equal weight tumor samples will be simultaneously infected with $1\times10^8$ ifu each Ad-INSM1prom-MetLuc and Ad-RSV-secreted alkaline phosphatase (SEAP) virus for normalization. Twenty-four hours later, the supernatant will be collected and the Met luciferase and SEAP activity sequentially measured using the Ready-To-Glow Secreted reporter assay (Clontech). The advantage to using secreted reporter genes is that the tumor biopsy remains live and intact and may be used in other assays such as antitumor efficacy studies using Ad-INSM1promHSVTk constructs.

Example 2

Effect of Modification of INSM1 Promoter Region with NRSEs in Non-INSM1 Expressing Cells The existing INSM1 promoter region has been modified to incorporate DNA elements from other tissue selective genes that have silenced expression of neuronal genes in non-neuronal cells. The first modification of the existing INSMI promoter region was addition of two tandem copies of the neuronal restrictive silencer elements (NRSEs) derived from the mouse nicotinic acetylcholine receptor (nAChR) or the rat superior cervical ganglion 10 (SCG10) promoters either directly upstream or downstream of the INSM1 promoter sequence. The NRSE elements when bound by the cognate protein, the neuron restrictive silencing factor, NRSF, can strongly repress transcription in non-neuronal cells as well as allow transcription of the same gene in neuronal cells. Transient transfection for comparison between the wild type 1.7 kbp INSM1 promoter with the SCG10 up or down, or n(AchR) up or down modifications were performed in a panel of INSM1 negative and INSM1 positive cell lines. In addition, the CT/CGRP gene is active in both the endocrine and the nervous systems (21-23).

The various INSM1 promoter constructs as described above were transiently transfected into HepG2 (hepatocellular carcinoma), HEK-293 (embryonic kidney), Cos7* (African green monkey kidney), or U87MG (glioblastoma) cells. These cell lines do not express detectable levels of INSM1 mRNA. The relative activity of the modified INSM1 promoter-luciferase constructs were compared directly to the control unmodified INSM1 promoter. Cells were assayed twenty four hours post transfection using the Dual-Glo luciferase reagent (Promega). A TK-renilla luciferase construct was included in all the wells for normalization of transfection efficiency. All transfections were performed in triplicate on at least three occasions. The results are shown in FIG. 1.

In the negative cell lines HepG2 (human hepatocellular carcinoma), HEK-293 (human embryonic kidney), Cos 7 (African green monkey kidney), and U87MG (human glioblastoma) cells, inclusion of the NRSE either upstream or downstream of the INSM1 promoter region repressed the activity of the INSM1 promoter although to different extents in the various cell lines. The repressive effect was dependent on the sequence of the NRSE and the relative position with respect to the INSM1 promoter.

The most dramatic effect was observed in the HepG2 cells. As shown in FIG. 1, addition of either the SCG10 or the nAChR NRSE either in the up or downstream positions resulted in a dramatic 90-95% reduction in the INSM1 promoter activity. This result demonstrated a significant benefit for the inclusion of an NRSE element with the INSM1 promoter to increase its tissue specificity. More importantly, adenovirus as well as other viral delivery vectors selectively infects the liver and damage to the liver is one of the major observed side effects of suicide gene therapy.

Analysis in other non-neuronal cell lines, HEK-293 kidney cells resulted in a reduction by 80-85% relative to the unmodified promoter constructs. Lastly, inclusion of the NRSE resulted in the reduction by 70-80% in the U87MG glioblastoma cells. Taken together, the net reduction in expression observed from the NRSE-INSM1 promoter constructs shows a clear benefit to the alteration of the INSM1 promoter to reduce any "leaky" or undesirable expression from the INSM1 promoter region in off-target cells.

Example 3

Figure 2:
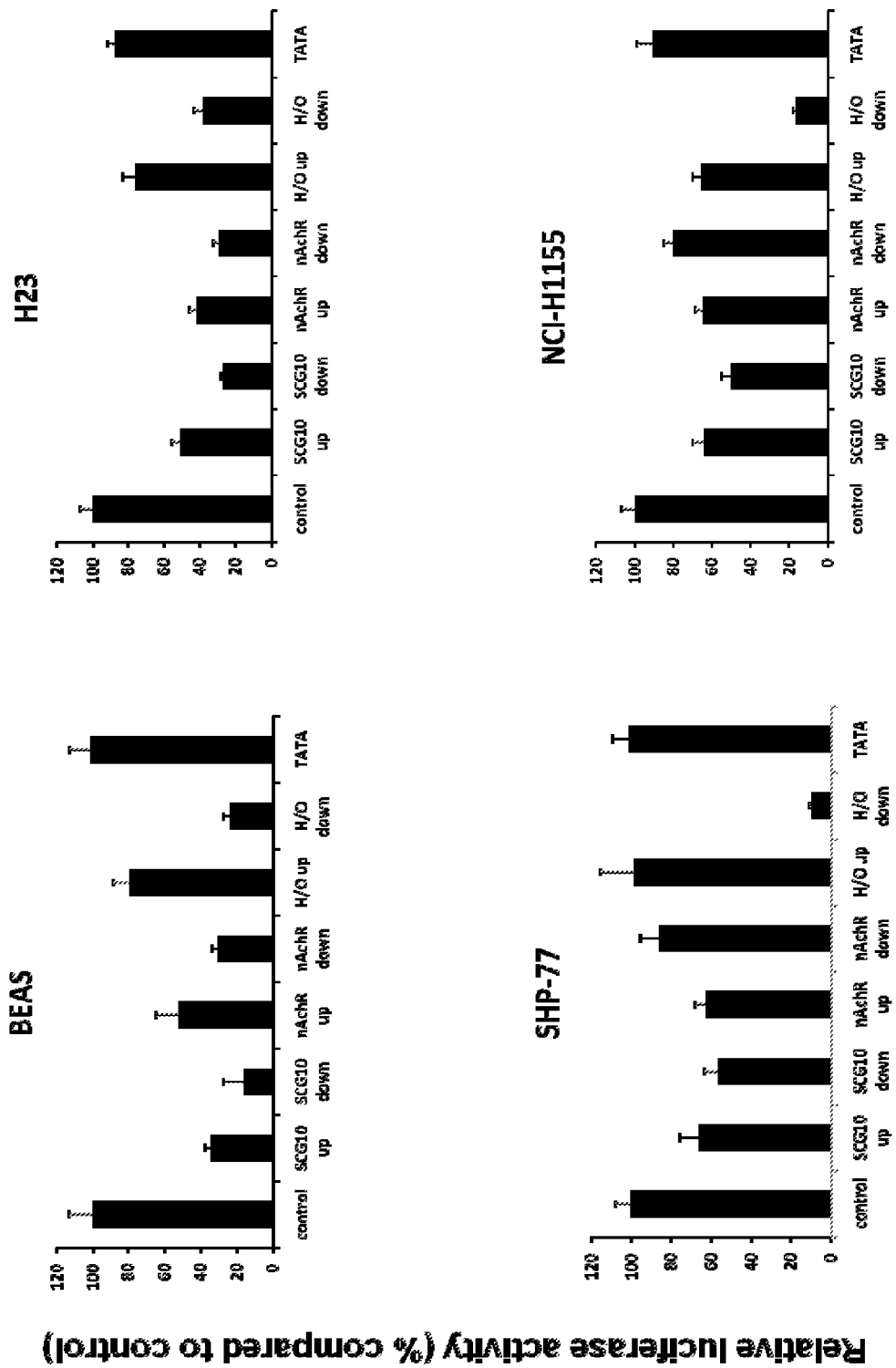
FIG. 2 illustrates the effect of various INSM1 promoter modifications on luciferase activity as compared to a control in several human lung cancer cell lines, i.e., in BEAS (normal bronchial epithelial cells), NCI-H23 (lung adenocarcinoma cells), SHP-77 (small cell lung cancer; SCLC) and NCI-H1155 (large-cell neuroendocrine carcinoma; LCNEC). All transient transfections were normalized with TK-renilla and performed in triplicate on three separate occasions.

Effect of Modification of INSM1 Promoter Region with NRSEs in INSM1 Expressing Cells The effect of the modified INSM1 promoter on INSM1 expressing cell lines was determined to see if the changes negatively affect the promoter in target cell types. One of the most prevalent and aggressive forms of neuroendocrine tumors is small cell lung cancer (SCLC). To assess the effect of the NRSE modifications on promoter activity, transient transfections were performed in a "normal" human bronchial epithelial cell line, BEAS, a human lung adenocarcinoma cell line, NCI-H23, and two human SCLC cell lines SHP-77 and NCI-H1155. In these four cell lines, the control INSM1 promoter luciferase construct was compared with the modified promoter constructs. All transient transfections were normalized with TK-renilla and performed in triplicate on three separate occasions. Luciferase activity was assessed using the Dual-Glo luciferase reagent (Promega). The results are shown in FIG. 2.

In the BEAS and NCI-H23 cells, addition of the either NRSE from the SCG10 or n(AchR) genes resulted in a reduction in activity of the INSM1 promoter. This result was anticipated since these cell lines neither exhibit neuronal characteristics nor express INSM1. Of note, in both the BEAS and H23 cells, both NRSE down constructs exerted a stronger reduction in the INSM1 promoter activity (~80-90%). Unexpectedly in the INSM1 positive cell lines SHP-77 and NCI-H1155, the NRSE constructs negatively affected INSM1 promoter activity ranging between 10-50%. Despite the reduction to overall promoter activity, closer inspection revealed that the nAChR down only modestly reduced promoter activity by 10-20% in the INSM1 positive SCLC cell lines. Re-evaluation of the 6 non-neuronal cell lines HepG2, HEK-293, Cos7, U87MG, BEAS, and H23 revealed that the n(AchR) NRSE downstream modification reduced the INSM1 promoter activity more dramatically than the other NRSE modifications. Despite the modest reduction to the INSM1 promoter activity in the SCLC cells, the dramatic suppression by 80-95% in non-neuronal or non-target cells would be beneficial to improve the safety of the suicide gene therapy approach.

Example 4

Figure 3:
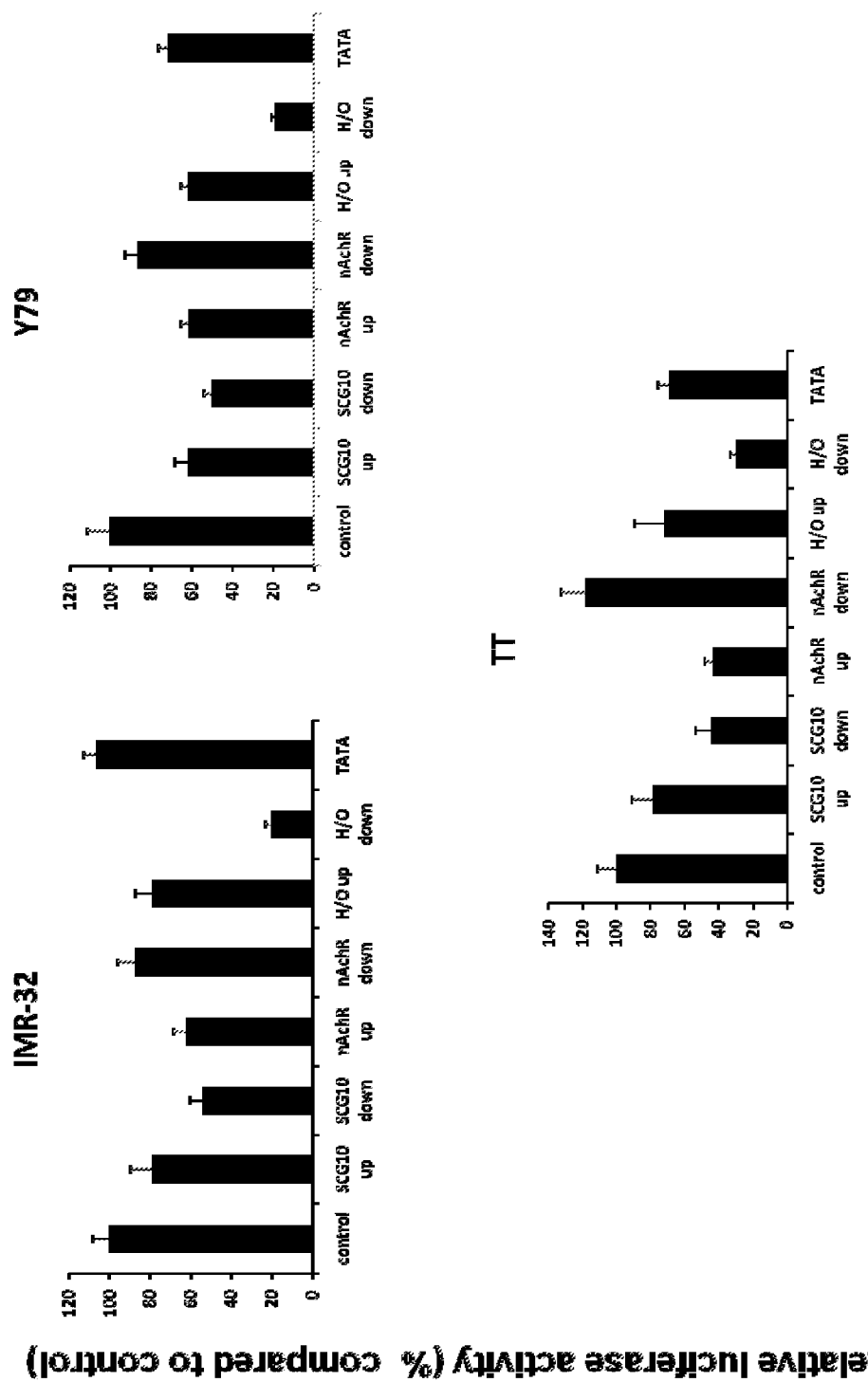
FIG. 3 illustrates the effect of various modified INSM1 promoter luciferase constructs at 24 hr post transfection as compared to a control in INSM1 positive tumors, i.e., in INSM1 positive human tumor cell lines, IMR-32 (neuroblastoma), Y79 (retinoblastoma), and TT (medullary thyroid carcinoma). All transfections were performed in triplicate on at least three separate occasions.

Effect of Modification of INSM1 Promoter Region with NRSEs in INSM1 Expressing Neuroendocrine Tumor Cells To verify that the NRSE element did not substantially affect the activity of the INSM1 promoter in other INSM1 positive neuroendocrine tumor cell lines, the unmodified and modified INSM1 promoter luciferase activity was compared in IMR-32 human neuroblastoma, Y79 human retinoblastoma, and TT human medullary thyroid carcinoma cell lines. Cells were assayed twenty four hours post transfection with the Dual-Glo luciferase kit (Promega). All transfections were performed in triplicate on at least three separate occasions. The results are shown in FIG. 3. Overall the various NRSE modifications lowered the INSM1 promoter activity by 10-60%. However, the 2×n(AchR) down construct activity showed only a modest reduction of the promoter activity in the IMR-32 (10%) and Y79 (15%) cells. In contrast, the n(AchR) NRSE down construct in the medullary thyroid carcinoma TT cells showed a modest increase (120%) in promoter activity.

Taken together, inclusion of the n(AchR) NRSE element downstream of the INSM1 promoter region was shown to significantly enhance the safety of the INSM1 promoter driven suicide gene therapy by reducing activity in non-desirable cells. At the same the modification had a minimal impact on the strength, activity, and specificity of the INSM1 promoter in neuroendocrine tumor cells.

Example 5

Effect of Modification of the INSM1 Promoter with H/O Enhancer

The sequence responsible for cell-specific expression of the CT/CGRP gene was characterized and designated the H/O enhancer. The H/O enhancer consists of an overlapping basic helix loop helix (bHLH) binding site and an octamer binding site (24;25). Therefore, this element was also used to modify the INSM1 promoter activity as described in Example 1, and tested for its effect in various endocrine and/or neuroendocrine carcinoma cells as described above for the other modified INSM1 promoters (Examples 1-4). The results for the various cell types are shown in FIGS. 1-3.

The H/O enhancer was not so successful. Disappointingly in all cell types tested, including non-neuronal (HepG2, HEK-293, U87MG, BEAS, H23) and neuroendocrine cells (SHP-77, H1155, IMR-32, Y79, and TT), inclusion of the H/O enhancer caused a reduction to the overall INSM1 promoter activity, as shown in FIGS. 1-3.

Example 6

Effect of Modification of INSM1 Promoter with Consensus TATA Box

Analysis of the INSM1 promoter sequence revealed that it consists of 66% GC nucleotides and does not contain a consensus TATA box a common characteristic of GC rich promoter sequences. Traditionally, a consensus TATA sequence recruits the TATA binding protein (TBP) as well as a host of accessory factors necessary for transcription initiation including the recruitment of RNA polymerase II. A sequence in the INSM1 promoter resembles a TATA binding site but contains a few nucleotide alterations as compared to the consensus. Therefore, an exchange of this non-conserved site into a consensus TATA box was conducted to analyze the effect on the increased rate of transcription initiation on the INSM1 promoter and thus on the increased rate in the overall promoter activity. The INSM1 sequence between nucleotides −34 to −27 base pairs were altered by site-directed mutagenesis and confirmed correct by sequence analysis as described in Example 1. The TATA modification was tested in a panel of INSM1 positive and negative cell lines as described above in Examples 1-4. As shown in FIGS. 1-3, the substitutions made to resemble a consensus TATA binding site did not show any significant change to the overall activity of the INSM1 promoter in any of the cell types analyzed.

Overall, the n(AchR) NRSE downstream element gave the best profile. In the transfections into non-neuronal cell types especially the liver the INSM1 promoter with the n(AchR) NRSE activity was barely measurable (5% of control) and significantly reduced in the kidney, glioma, and normal lung epithelial cells. Conversely, despite a slight decrease 10-20% in the overall INSM1 promoter activity in the INSM1 positive tumor cells the benefit of the reduction of the off-target activity in non-expressing cells far outweighs the small decrease observed.

Example 7

In Vivo Treatment of Tumors with Virus with INSM1 Promoter Linked to Toxin

Figure 4A:
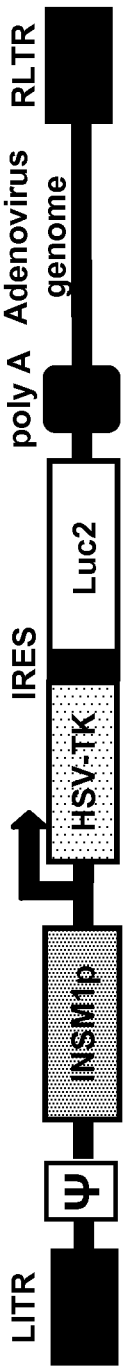
FIG. 4A is a schematic diagram of configuration of the INSM1 promoter HSV-Tk-Luciferase 2 gene in the adenovirus genome.

To deliver the gene therapy into the target tumor cells a viral delivery system was used. A first generation E1/E3 deleted non-replicating Ad5 vector was used, but other forms of viral delivery systems could be used. The unmodified 1.7 kilobase pair INSM1 promoter was linked directly with the herpes simplex virus thymidine kinase gene (the toxin) and firefly luciferase gene (separated by an internal ribosomal entry site and incorporated into the adenoviral genome, creating Ad-INSM1p-HSV-tk IRESLuc2 (Control). FIG. 4A is a schematic diagram showing the configuration of the INSM1 promoter HSV-Tk-Luciferase 2 gene in the adenovirus genome. Inclusion of the firefly luciferase 2 gene allowed the simultaneously monitoring of the promoter activity and the relative killing effect using a non-invasive in vivo imaging system (e.g., Kodak Multispectral In Vivo FX). SCLC cell lines were used for the tumors since this tumor represents one of the more prevalent neuroendocrine tumor for treatment. To detect the tumor cells non-invasively in a subcutaneous animal model, the NCI-H1155 cells were transduced with a lentivirus expressing red Cherry fluorescent protein as described in Example 1. The fluorescent cells were sorted using a fluorescence activated cell sorter to obtain a pure population.

Figure 4B:
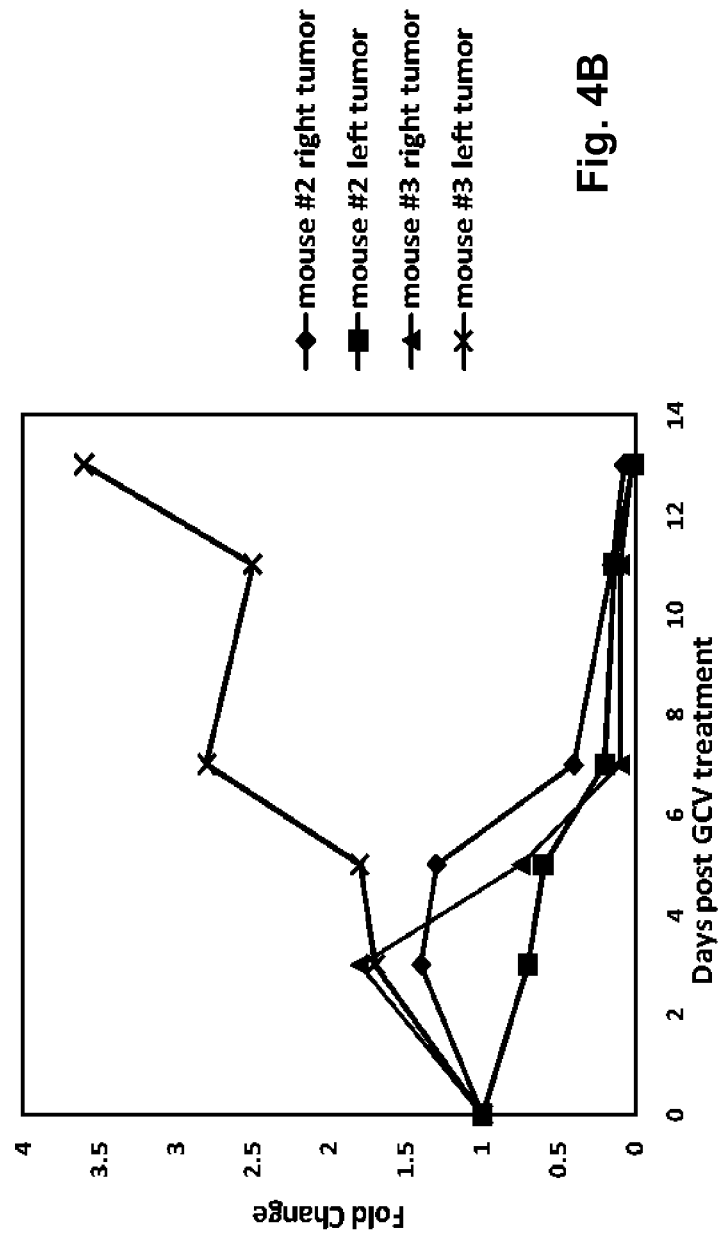
FIG. 4B depicts change in tumor size as a function of time following gene therapy and administration of ganciclovir, for two tumors in each of two mice (four tumors total).

Subsequently, $1 \times 10^6$ NCI-H1155 Red cells were transplanted subcutaneously into 8-week-old male nude mice on both hind flanks. The tumors were allowed to form for 10 days before the gene therapy was initiated. To start the gene therapy, the animals were given a single intratumoral $1 \times 10^9$ ifu injection of Ad-INSM1p-HSVtkIRESLuc2 virus. Twenty four hours post virus administration, intraperitoneal injections of 50 mg/kg body weight ganciclovir (Cytovene-IV, Roche Genentech, San Francisco, Calif.) were given daily for 14 days. The tumors were monitored by both caliper measurements and in vivo imaging. As shown in FIG. 4B, three out of the four tumors completely regressed during the treatment period. One tumor in mouse #3 completely failed treatment and continued to grow as measured with the caliper.

Additionally, the animals were monitored using non-invasive in vivo imaging. The animals were immobilized using isoflurane inhalation anesthesia prior to imaging. The animals were imaged for red fluorescent signal to set a baseline for the tumor on Day 0 prior to the start of therapy (FIGS. 5A and 6A). Ten minutes before imaging, the animals received a 100 µl intraperitoneal injection of 15 mg/ml D-luciferin substrate. The animals were then photographed for fluorescence, luminescence, and X-ray to establish an anatomical reference for the animals (FIGS. 5B and 6B). Results for Mouse #2 and Mouse #3 are shown in FIGS. 5 and 6, respectively.

For Mouse #2, both hind flank tumor masses are clearly visible on Day 0 prior to therapy. Following injection of the virus, a strong luciferase signal can be detected in both tumor locations from mouse #2 (FIG. 5B). By day 11, the fluorescence image from Mouse #2 from both tumor masses was barely detectable (FIG. 5A). Conversely, a strong luciferase signal is seen in both of the tumor masses in Mouse #2 throughout the treatment (FIG. 5B). This result indicates the efficacy of the treatment for SCLC.

Despite the robust response observed with Mouse #2, Mouse #3 had one tumor mass that completely regressed and one tumor that was completely unresponsive to the therapy. Imaging of Mouse #3 gave some important insight into why this tumor failed the therapy. The left side tumor in Mouse #3 completely disappeared following a single intratumoral virus injection by Day 7 and had a corresponding strong luciferase signal on Days 3 and 5 (FIGS. 6A and 6B). In contrast, the right hand tumor, upon closer inspection had only a small weak luciferase signal on day 3 that has completely diminished by day 5 (FIG. 6B). Therefore, imaging revealed that the lack of response in Mouse #3's right side tumor was due to improper delivery of the virus into the tumor mass. This observation highlighted the value of in vivo imaging, and indicated that the gene therapy did not fail due to lack of efficacy but rather due to experimental error. These results unequivocally demonstrate that the Ad-INSM1p-HSV-tkIRESLuc2 therapy is effective for the treatment of SCLC tumors when injected intratumorally.

Figures 7A, 7B:
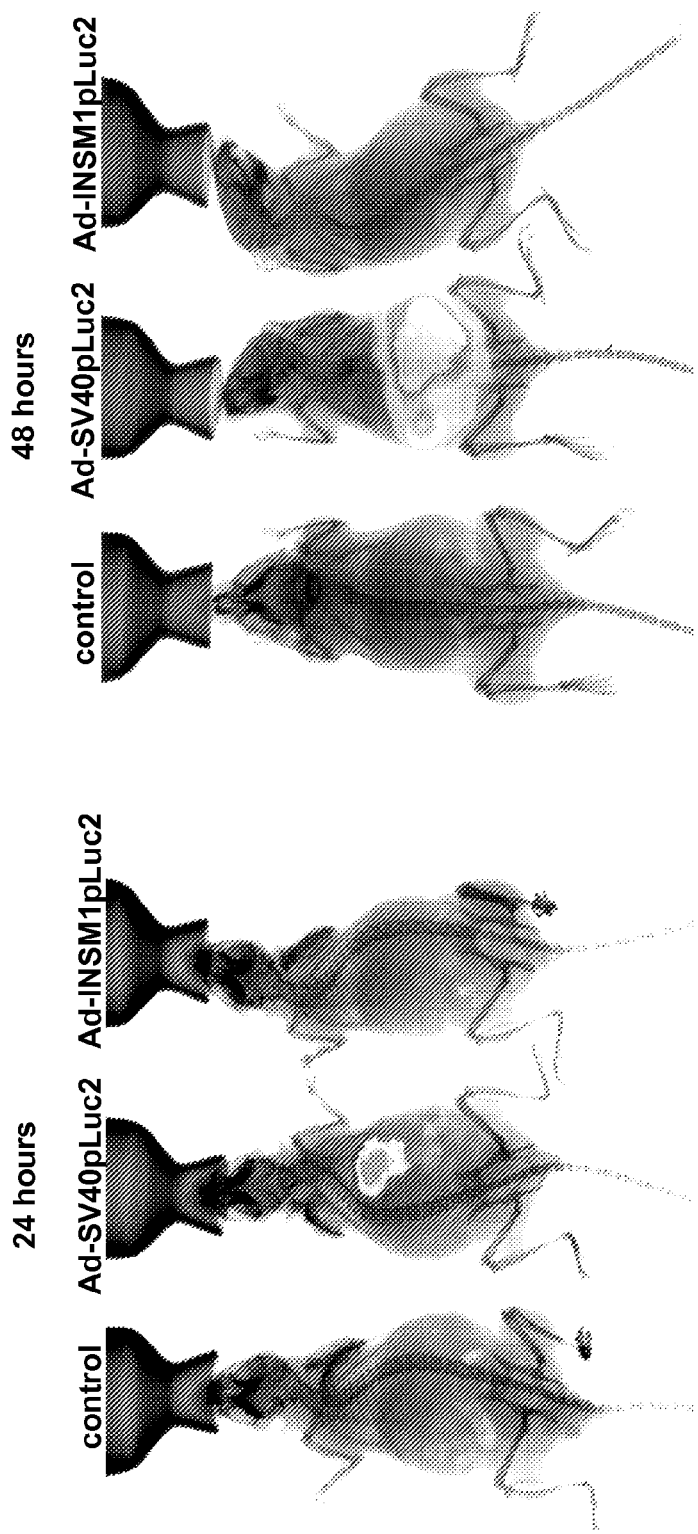
FIG. 7A illustrates the in vivo imaging showing the biodistribution of two different constructs, Ad-SV40Luc2 and Ad-INSM1pLuc2 virus in naïve animals at 24 hr following a single 1×10⁹ ifu of either Ad-SV40Luc2 or Ad-INSM1p-Luc2 virus injected intraperitoneally into BALB/c mice. The animals were given 100 μl 15 mg/ml D-luciferin and imaged for luminescence signal and X-ray.
FIG. 7B illustrates the in vivo imaging showing the biodistribution of two different constructs, Ad-SV40Luc2 and Ad-INSM1pLuc2 virus in naïve animals at 48 hr following a single 1×10⁹ ifu of either Ad-SV40Luc2 or Ad-INSM1p-Luc2 virus injected intraperitoneally into BALB/c mice. The animals were given 100 μl 15 mg/ml D-luciferin and imaged for luminescence signal and X-ray.

Systemic delivery of suicide gene therapy has some advantages, and systemic delivery of the suicide gene constructs into naïve or non-tumor bearing animals was tested to determine its effectiveness. To test the promoter specificity or tissue distribution, BALB/c mice were given a single $1 \times 10^9$ ifu intraperitonel (i.p.) injection of phosphate buffered saline (PBS; control), Ad-SV40p-Luc2 or Ad-INSM1p-Luc2 adenovirus. Twenty-four and forty-eight hours post virus injection, the animals were given 100 µL 15 mg/ml D-luciferin and anesthetized with isoflurane. The animals were imaged for luminescence and with X-ray for an anatomical reference, and the results shown in FIGS. 7A (24 hr) and 7B (48 hr). At 24 hours, no luciferase signal was detected from either the PBS or Ad-INSM1p-Luc2 mice (FIG. 7A). However, a strong signal from the lower abdomen around the liver and kidney region was readily detected from the Ad-SV40p-Luc2 animal (FIG. 7A, center mouse). A similar profile was noted at 48 hours except the signal from the Ad-SV40-Luc2 mouse covered a broader region of the abdomen and the signal was more intense (FIG. 7B, center mouse).

Figure 8:
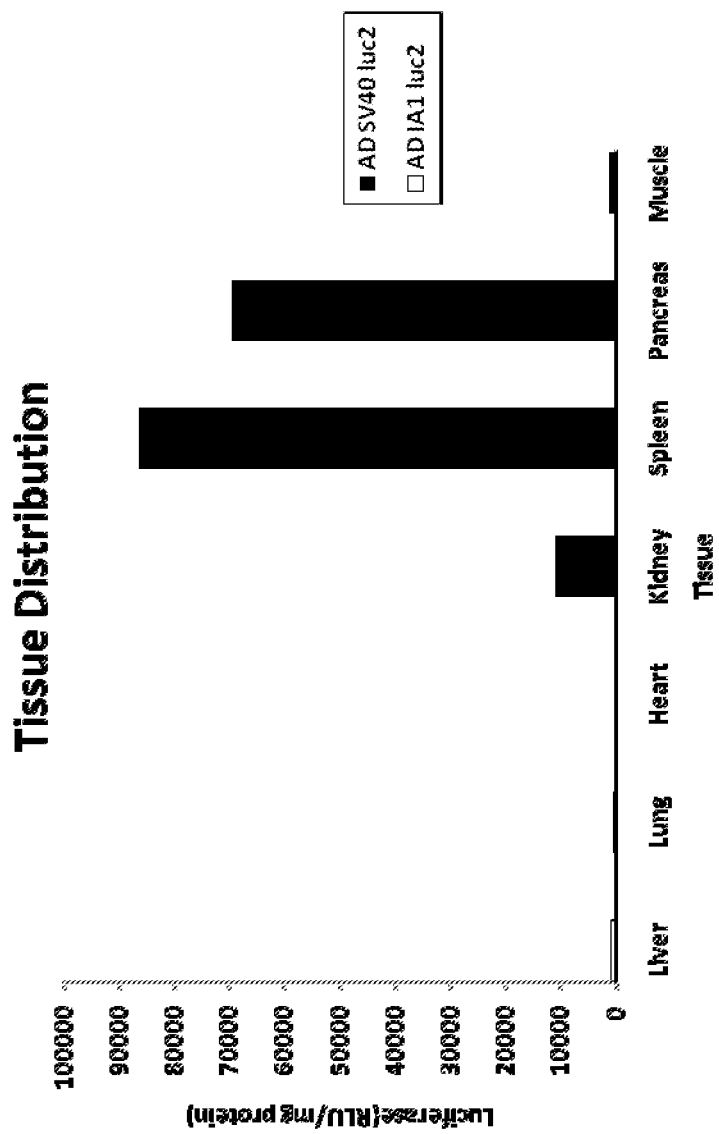
FIG. 8 illustrates the amount of luciferase activity (normalized against total protein from each tissue) from mice injected with either the Ad-SV40Luc2 or the Ad-INSM1pLuc2 virus as found in various animal tissue homogenates forty eight hours following initial virus injection. The animals were sacrificed, tissues removed, homogenized in a luciferase assay buffer, and luciferase activity was measured.

Following the 48-hour time point, the animals were sacrificed by $CO_2$ inhalation, and various organs removed and snap frozen on dry ice. The tissues were homogenized in 1 ml luciferase assay buffer and assayed for luciferase activity. The luciferase activity was normalized against total protein in the assay, and the results are shown in FIG. 8. Tissues from the Ad-SV40Luc2 mice had strong measurable luciferase activity from the spleen, pancreas, and kidney. The peak luciferase activity measured in vitro correlated with the location of the luciferase signal observed by in vivo imaging in the Ad-SV40p-Luc2 mouse. Critically, as shown in FIG. 8, no appreciable luciferase activity was detected from the Ad-INSM1p-Luc2 collected tissues. Therefore, the in vivo imaging and in vitro luciferase assay from isolated tissue homogenates reveal that systemic administration of the INSM1 promoter gene therapy would be safe due to the absence of detectable luciferase activity in normal tissues in the naïve animals.

Example 8

New Constructs to Increase Tissue Specificity of INSM1 Promoter and In Vitro Testing Interference from the viral backbone with respect to the tissue selectivity of the promoter incorporated into the viral vectors has been found. To prevent the adenoviral sequences from potentially interrupting the INSM1 promoter activity, other constructs were made and tested. In other studies, the adenovirus left inverted terminal repeat (ITR) sequence was shown to have strong transcriptional initiation activity (26). Potential ways to negate all outside influences on tissue specific promoter activity is to change the location of the INSM1 promoter in the adenovirus backbone and/or flank the INSM1 promoter driven expression cassette on either end with the chicken β⁻-globin HS4 insulator sequence. The new constructs were made as described in Example 1, and are schematically shown in FIG. 9. Insulators are DNA elements that have the ability to protect genes from inappropriate signals originating from the surrounding environment by acting as a physical barrier or boundary. The chicken β⁻-globin HS4 insulator element has been shown to block the actions of enhancer elements in addition to functioning as a physical boundary that can prevent the spread of gene silencing (20; 27-32). Shown in FIG. 9 are the constructs that have been cloned into the luciferase reporter vector (pGL4 Promega) and transferred into the adenoviral backbone (Ad-Easy XL, Agilent) that either alter the location of the INSM1 promoter constructs and/or include insulator elements.

Transient transfections were performed as described above to test the constructs in vitro to determine if the insulator and/or the insulator and the NRSE sequences protect the INSM1 promoter without intervening with its activity and specificity. The constructs tested include the original INSM1 promoter (CLuc2; Control), the INSM1 promoter containing the NRSE that is cloned in the opposite orientation with respect to the original control (C1Luc2; C1), the INSM1 promoter with the HS4 insulator at 5' end (C2Luc2; C2), the INSM1 promoter and 2×NRSE with two tandem copies of the HS4 insulator at the 5' end (M2Luc2; M2) and the INSM1 promoter containing the NRSE cloned in the opposite orientation and flanked on both the 5' and 3' ends with the HS4 insulator (M3Luc2; M3).

Figure 10:
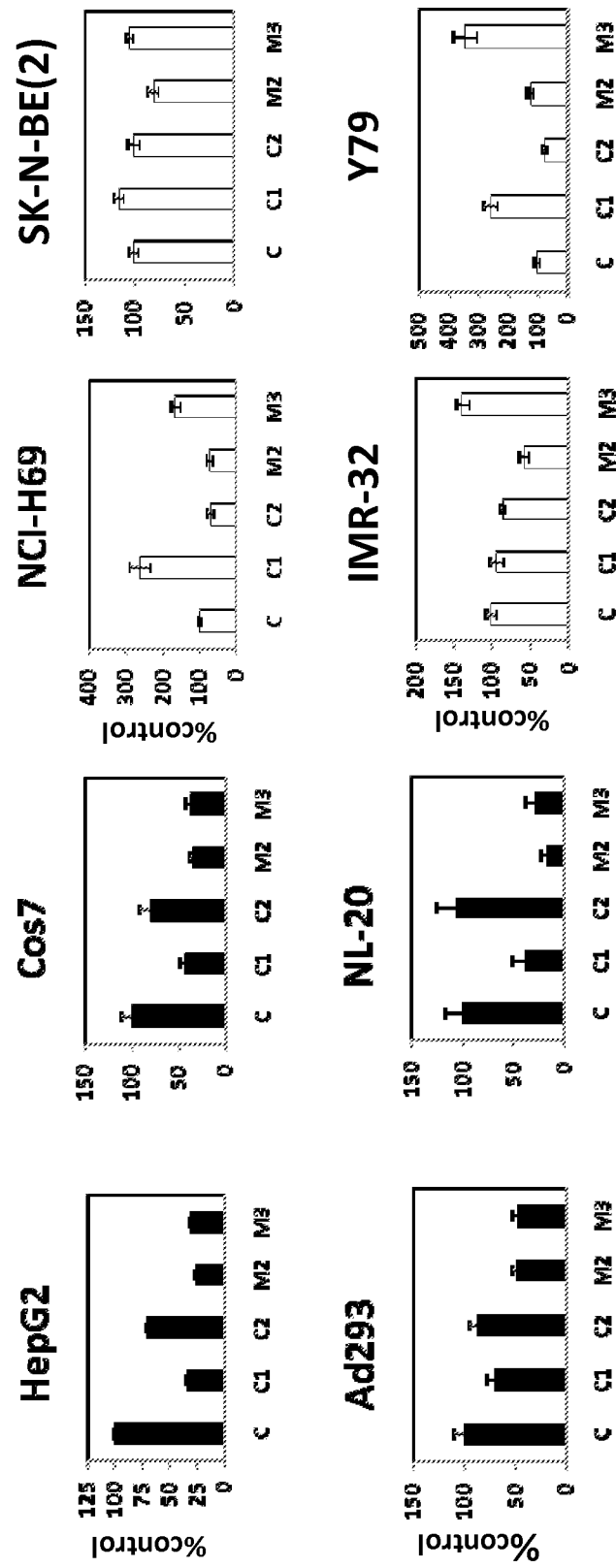
FIG. 10 illustrates the % luciferase assay in several INSM1 negative cell lines (HepG2, Cos7, Ad293, and NL-20 black bars) and INSM1 positive cell lines (NCI-H69, SK-N-BE(2), IMR-32, and Y79 white bars) when transfected C, C1, C2, M2 or M3 constructs. All assays were performed in triplicate at least three times. All graphs were plotted relative to the original INSM1 promoter luciferase constructs (% control, C).

A panel of INSM1 negative cells lines (liver (HepG2), kidney (Cos7 and HEK-293), and lung epithelium (NL-20)) and INSM1 positive cell lines (SCLC (H69), neuroblastoma (SK-N-BE(2), IMR-32), and retinoblastoma (Y79)) were transiently transfected. The results are shown in FIG. 10. All assays were performed in triplicate at least three times. All the constructs are graphed relative to the control unmodified INSM1 promoter (C) that was fixed at 100%. C2Luc2 was the only construct that did not contain the 2×NRSE modification but contained a 5' HS4 β-globin insulator element. In both the INSM1 negative (black bars) and positive (white bars) cell lines shown in FIG. 10, the activity of the C2Luc2 construct was similar to the original INSM1 promoter construct in the presence of the HS4 insulator sequence. Consequently, this indicates that inclusion of the insulator sequence does not alter the INSM1 promoter activity or specificity. However, all of the NRSE containing constructs (i.e., C1Luc2, M2Luc2, and M3Luc2) were significantly lower with respect to the control INSM1 promoter in the INSM1 negative cell lines (FIG. 10, black bar graphs). Alternatively, in the INSM1 positive cell lines, the C1 and M3 constructs maintained the same activity as the control in the H69 and H1155 cells. However in the Y79 and IMR-32 cells, the M3 constructs had a 1.5-3 fold higher activity (FIG. 10, white bar graphs). Interestingly, incorporation of two tandem copies of the HS4 insulator at the 5' end of the INSM1 promoter construct (M2) reduced promoter activity relative to the control in the INSM1 positive cells lines (FIG. 10, comparison of C to M2; black bar graphs). Therefore, this construct was removed from further evaluation. The in vitro results clearly demonstrate that the inclusion of a single upstream or both an upstream and downstream copy of an insulator does not alter the INSM1 promoter transcriptional activity. In addition, the results demonstrate that incorporation of the 2×NRSE reduced INSM1 activity in a panel of INSM1 negative cells, but enhanced promoter activity in two INSM1 positive cell lines (IMR-32 and Y79).

Example 9

Effectiveness of Insulated, Modified INSM1 Promoter in Adenoviral Genome

An experiment was conducted to test the insulated, modified constructs in adenovirus. Due to the 7.5 kilobase pair size limit for the insertion of an expression cassette into the adenoviral genome, the insulator modified INSM1 promoter linked with both the luciferase and the HSVtk gene cannot be incorporated into the same virus. As a result, separate adenoviral constructs containing either the luciferase or HSVtk gene was generated for testing in vitro and in vivo. The first adenovirus construct that was successfully generated and tested is the Ad-C2Luc2 construct (C2, FIG. 9). The C2Luc2 construct is the original INSM1 promoter containing an insulator sequence separating it from the viral LITR but lacking the nAChR derived NRSE elements.

The control (Ad-INSM1pLuc2) or C2Luc2 (Ad-HS4ins-INSM1pLuc2) viruses were injected into tumor bearing mice as described above in Examples 1 and 7. Eight-week-old male nude mice (three groups of three mice each) were injected subcutaneously with $1 \times 10^6$ NCI-H1155 Cherry fluorescent tumor cells into the hind flanks and grown for 10-14 days. Following tumor establishment, the animals were injected via intravenous (IV), intraperitoneal (IP), or intratumoral (IT) injection with $1 \times 10^9$ ifu Ad-control or Ad-C2Luc2 virus. Forty-eight hours post virus administration, the animals were sacrificed and the lung, liver, kidney, pancreas, spleen, and tumors were collected. The cell lysates were homogenized in glo-lysis buffer (Promega), and luciferase activity was measured and normalized with total tissue protein. The results are shown in FIG. 11 which shows the average of the three animals plotted as relative light units normalized for mg total protein (Black bars=IT injection; white bars-IV injection; and hatched bars=IP injection).

Figure 11:
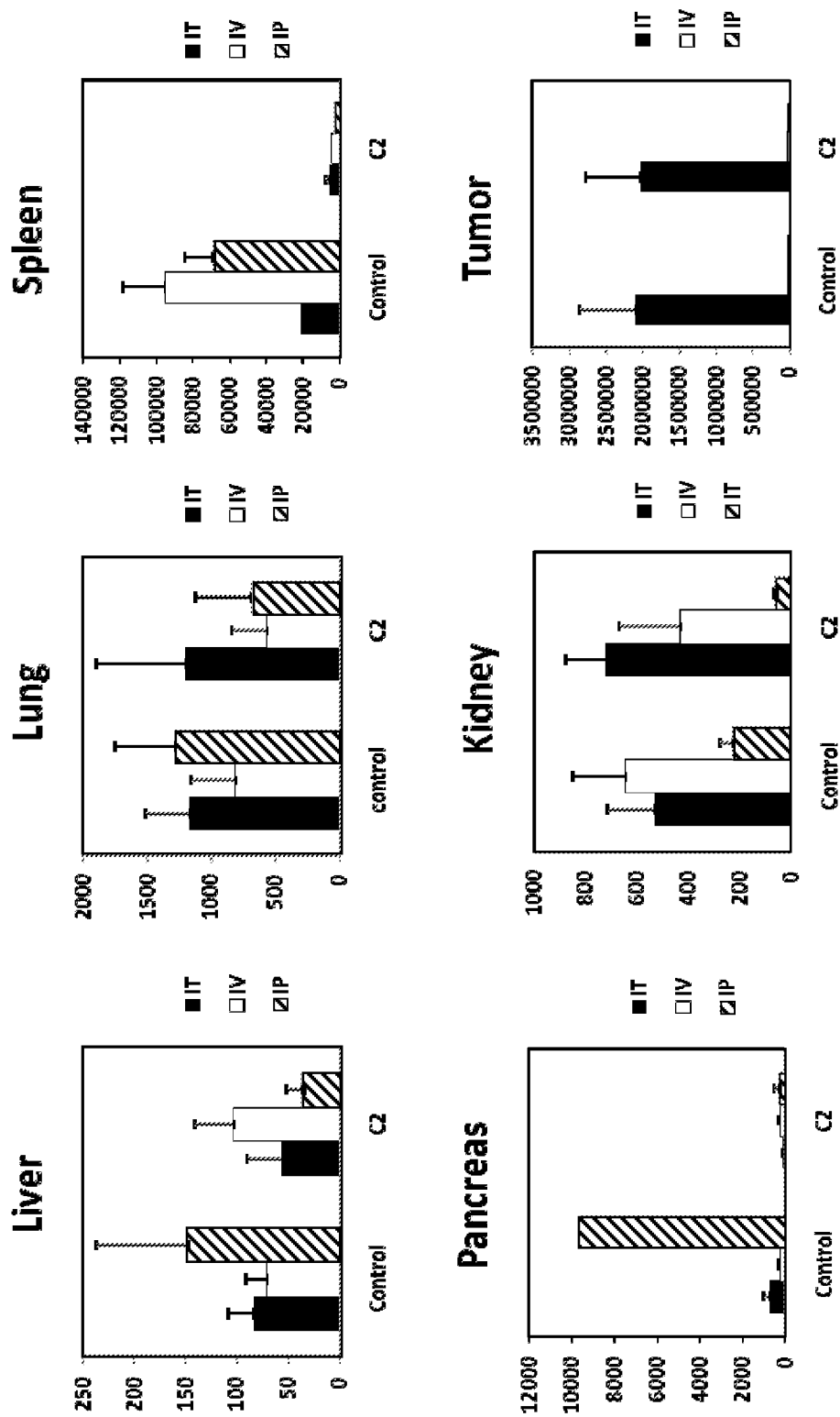
FIG. 11 illustrates the relative luciferase activity in tissues collected from eight week old male nude mice of several different injection routes (IT, intratumoral; IV, tail-vein; and IP, intraperitoneal) of 1×10⁹ ifu AdINSM1p-Luc2 (control) or ADHS4insINSM1p-Luc2 (C2) adenovirus, injections occurring two weeks after the mice were injected with 1×10⁶ NCI-H1155 tumor cells. Forty eight hours post injection, the animals were sacrificed, and the tissues (liver, lung, spleen, pancreas, kidney, and tumor) collected, homogenized, and analyzed for luciferase activity. Shown in FIG. 11 is the average of the three animals plotted as relative light units normalized for mg total protein (black bars=IT injection; white bars=IV injection; and hatched bars=IP injection).

Comparison of the tissues collected from the IV group indicated luciferase activity in the control group was strongest in the spleen, followed by the lung and the kidney (FIG. 11, white bars). The other tissues (Liver, Pancreas, and Tumor) did not show luciferase activity significantly higher than the non-specific background activity. The Ad-C2Luc2 group had no detectable luciferase activity in the Spleen, and the luciferase activity was reduced by ~40% in the Lung and Kidney relative to the Ad-INSM1 Luc2 control (FIG. 11, white bars). Similarly in the IP group, the Ad-INSM1 Luc2 control virus had the strongest luciferase activity in the spleen, followed by the pancreas, and the lung (FIG. 11, hatched bars). Intriguingly, in the IP group, the Ad-C2 Luc2 activity was completely abolished in both the spleen and pancreas and reduced by 60% compared to Ad-INSM1 Luc2 control in the lung (FIG. 11, hatched bars). Lastly, the IT animals with the Ad-INSM1 Luc2 control virus showed the spleen with the highest activity excluding the tumor, followed by the lung, the pancreas, and the kidney (FIG. 11, black bars). Interestingly, in the Ad-C2Luc2 IT group, the activity in the spleen was reduced by 75%, the pancreas activity was completely abolished, but the level in the lung remained the same. In contrast to the almost complete reduction of off-target luciferase activity in the spleen and pancreas, the kidney was slightly higher than the control group (FIG. 11, black bars). The most important observation for the IT group was that the tumor maintained the highest activity, indicating that the insulator element does not interfere with the INSM1 promoter specificity or activity. Therefore, this clearly demonstrates that the HS4 insulator located between the LITR and the INSM1 promoter can significantly reduce or eliminate any potential transcriptional interference from the adenoviral sequences in vivo and at the same time not alter the INSM1 promoter activation in the tumor cells.

Despite the observation of off-target activity of the original INSM1 promoter, the spleen was the only tissue that was significantly high. The Ad-C2Luc2 construct clearly demonstrated that the incorporation of the insulator element between the INSM1 promoter and the adenoviral backbone eliminated the activation in spleen. Therefore, the new configuration of the INSM1 promoter element in the adenoviral backbone with the incorporation of both the HS4 insulator element and nAChR NRSE elements will significantly improve the specificity of the INSM1 promoter driven cancer gene therapy.

The Ad-C1Luc2 and Ad-M3Luc2 viruses are in the final stages of amplification and will be tested as shown above for C2 in mice shortly. Complementary HSVtk viruses are also currently being developed as described in Example 1. Given the results obtained in animals, without wishing to be bound by this theory, it is believed that the adenovirus construct with the most promising outcome will be the Ad-M3Luc2 and Ad-M3HSVTk because it includes the 2×NRSE n(AchR) element and the expression cassette is flanked on both sides by the HS4 insulator elements. Additionally, the INSM1 promoter has been located further away from the potentially interfering LITR adenoviral sequence. Once these new constructs are obtained, the Ad-INSM1 HSVtk constructs will be tested first in vitro to determine their "killing" efficiency in a panel of INSM1 positive cell lines as described above in Example 1. The final step will be to verify the in vivo anti-tumor efficacy in nude mice as described above and in Examples 1 and 7.

Example 10

Effectiveness of Modified INSM1 Promoter as Diagnostic Tool

Figure 12B:
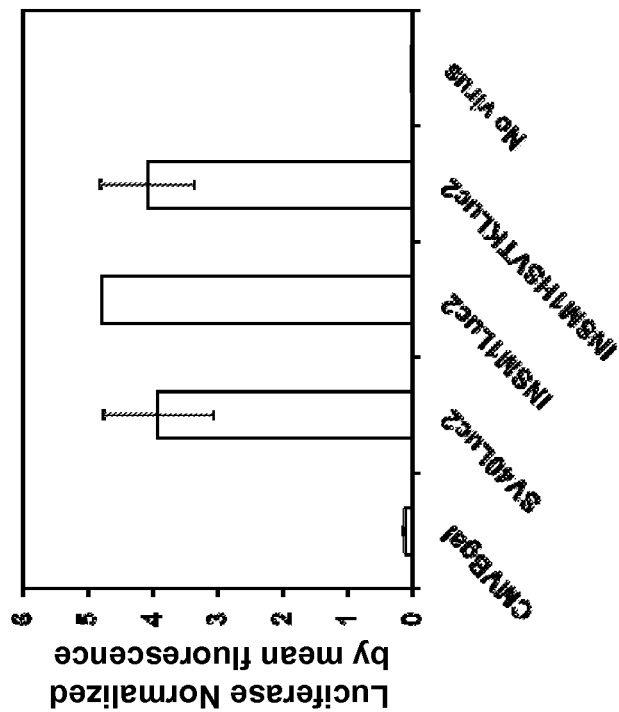
FIG. 12B illustrates the in vitro luciferase activity in tumor slices obtained from male nude mice ten days after injection with 1×10⁷ NCI-H1155 red fluorescent tumor cells, and luciferase activity measured 24 hours after the tumor slices were infected with 4×10⁸ ifu Ad-CMV-LacZ, Ad-SV40-Luc2, Ad-INSM1p-Luc2, or Ad-INSM1p-HSV-TkIRES-Luc2 viruses and after 10 min incubation in the presence of 5 μl 3 mg/ml D-luciferin substrate. The graph represents the luciferase activity divided by the mean fluorescence of the tumor slice for normalization.
Figure 12A:
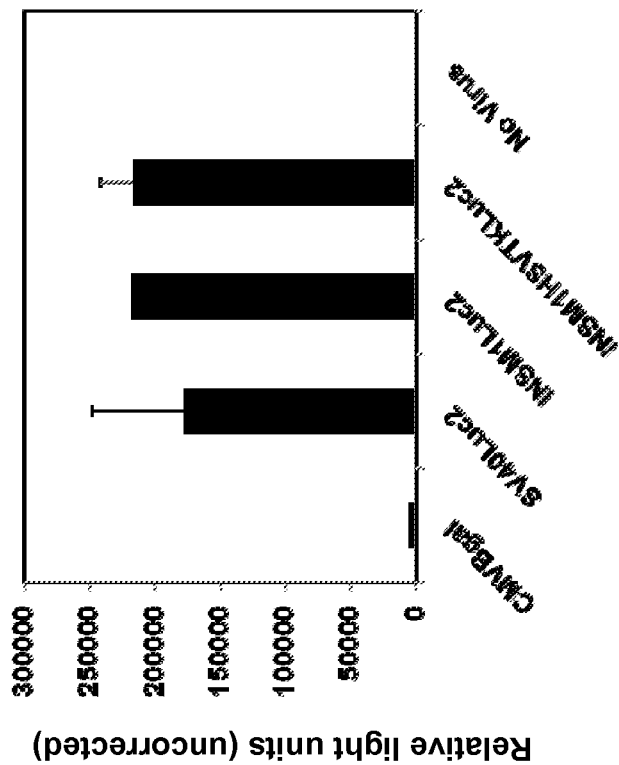
FIG. 12A illustrates the in vitro luciferase activity in tumor slices obtained from male nude mice ten days after injection with 1×10⁷ NCI-H1155 red fluorescent tumor cells, and luciferase activity measured 24 hours after the tumor slices were infected with 4×10⁸ ifu Ad-CMV-LacZ, Ad-SV40-Luc2, Ad-INSM1p-Luc2, or Ad-INSM1p-HSV-tkIRES-Luc2 viruses and after 10 min incubation in the presence of 5 μl 3 mg/ml D-luciferin substrate. The graph is the average of the relative light units as measured from the plate reader (not corrected for fluorescence).

Another application for the modified INSM1 promoter is as a diagnostic tool for the identification or verification of the presence of neuroendocrine tumors either from a biopsy specimen or to detect a tumor in a patient. To show the feasibility of this approach, an in vitro assay was performed using methods described in Example 1 and below. Using either the Ad-INSM1p-Luc2 or Ad-INSM1p-HSV-tkIRESLuc2 (suicide gene) constructs, the luciferase activity was compared to the Ad-CMV-LacZ negative control and the Ad-SV40-Luc2 positive controls in the NCI-H1155 xenograft tumor specimen. To generate a tumor specimen for the study, $1 \times 10^7$ NCI-H1155 red fluorescent tumor cells were injected subcutaneously into the hind flank of a male nude mouse. The tumors were allowed to form for 10 days. Following tumor formation, the animals were anesthetized; and the xenograft tumors were removed. Using a razor blade, small tumor pieces were cut and placed into a white, 96-well culture dish with RPMI 1640 media containing 10% fetal bovine serum (FBS). The tumor slices were infected with $4 \times 10^8$ ifu Ad-CMV-LacZ, Ad-SV40-Luc2, Ad-INSM1p-Luc2, or Ad-INSM1p-HSV-tkIRES-Luc2 viruses. Twenty-four hours post virus infection, red fluorescence was read on a BioTek Fluorescence plate reader. Each well was then incubated for 10 min in the presence of 5 µl of 3 mg/ml D-luciferin substrate; and luminescence readings were performed on a TopCounter NXT. The data was graphed in two different ways for comparison, and the results shown in FIGS. 12A and 12B. The first graph indicated the average of the duplicate wells relative to light unit measurement for each of the treatment groups (FIG. 12A). In the second approach, the luciferase readings were normalized against the fluorescence readings to account for any differences in activity due to the size of the tumor slice size (FIG. 12B). Due to the selectivity of the INSM1 promoter, a neuroendocrine tumor should be detected based on the activation of the reporter gene.

The Ad-INSM1pLuc2 and the Ad-INSM1p-HSV-tkIRESLuc2 constructs both showed similar levels of luciferase activity in the tumor slice, and was as strong if not stronger than the activity measured for the Ad-SV40-Luc2 virus. In addition, the overall relative luciferase activity between the non-corrected and fluorescence corrected samples was almost identical (FIGS. 12A and 12B). These data support the utility of the constructs for use in neuroendocrine tumor diagnostics.

For in vivo diagnostics, the suicide gene could serve a dual purpose. Several radiolabed [$^{18}$F]-labeled nucleotide analogs are currently available for the detection of HSV-tk activity (33). The radioactive nucleotide analogs for HSV-1 thymidine kinase will be administered, and the tumor cell expressing HSV-tk from the INSM1 promoter sequence will become phosphorylated and trapped leading to a quantifiable amount of radionucleotide accumulating within the tumor mass that could be visualized using a positron emission tomography (PET) scan or other known detector. One advantage to this detection system would be that the injection used for reporting is also being used for treatment. For future diagnostic experiments, the newly modified INSM1 promoter constructs containing the HS4 insulator and the 2×NRSE n(AchR) element will be used and linked directly with the HSVTk gene or the luciferase2 (Promega) or Metridia luciferase enzymes for in vitro diagnostics (Clontech). It is expected that these new constructs will perform equal to or better than described above for the Ad-INSM1p-HSV-tkIRESLuc2.

We have demonstrated an improvement to the specificity of the INSM1 promoter that can direct expression of a therapeutic gene for the treatment of neuroendocrine tumors. Additionally, by coupling the INSM1 promoter with a detectable reporter gene, this strategy can also be applied for the diagnosis of new onset or recurrent neuroendocrine cancers either from a tumor biopsy or in the patient directly.

REFERENCE LIST

1. Lan, M. S. and Breslin, M. B. (2009) *FASEB J.* 23, 2024-2033
2. Breslin, M. B., Zhu, M., and Lan, M. S. (2003) *J. Biol. Chem.* 278, 38991-38997
3. Duggan, A., Madathany, T., de Castro, S. C., Gerrelli, D., Guddati, K., and Garcia-Anoveros, J. (2008) *J. Comp Neurol.* 507, 1497-1520
4. Goto, Y., De Silva, M. G., Toscani, A., Prabhakar, B. S., Notkins, A. L., and Lan, M. S. (1992) *J. Biol. Chem.* 267, 15252-15257
5. Mellitzer, G., Bonne, S., Luco, R. F., Van De, C. M., Lenne-Samuel, N., Collombat, P., Mansouri, A., Lee, J., Lan, M., Pipeleers, D., Nielsen, F. C., Ferrer, J., Gradwohl, G., and Heimberg, H. (2006) *EMBO J.* 25, 1344-1352
6. Xie, J., Cai, T., Zhang, H., Lan, M. S., and Notkins, A. L. (2002) *Genomics* 80, 54-61
7. Goto, Y., De Silva, M. G., Toscani, A., Prabhakar, B. S., Notkins, A. L., and Lan, M. S. (1992) *J. Biol. Chem.* 267, 15252-15257
8. Lan, M. S., Russell, E. K., Lu, J., Johnson, B. E., and Notkins, A. L. (1993) *Cancer Res.* 53, 4169-4171
9. Taniwaki, M., Daigo, Y., Ishikawa, N., Takano, A., Tsunoda, T., Yasui, W., Inai, K., Kohno, N., and Nakamura, Y. (2006) *Int. J. Oncol.* 29, 567-575
10. Breslin, M. B., Zhu, M., and Lan, M. S. (2003) *J. Biol. Chem.* 278, 38991-38997
11. Li, Q., Notkins, A. L., and Lan, M. S. (1997) *Biochem. Biophys. Res. Commun.* 236, 776-781
12. Pedersen, N., Pedersen, M. W., Lan, M. S., Breslin, M. B., and Poulsen, H. S. (2006) *Cancer Gene Ther.* 13, 375-384
13. Wang, H. W., Breslin, M. B., Chen, C., Akerstrom, V., Zhong, Q., and Lan, M. S. (2009) *Hum. Gene Ther.* 20, 1308-1318

14. Hanawa, H., Yamamoto, M., Zhao, H., Shimada, T., and Persons, D. A. (2009) *Mol. Ther.* 17, 667-674
15. Guglielmi, L., Le, B. M., Truffinet, V., Cogne, M., and Denizot, Y. (2003) *Biochem. Biophys. Res. Commun.* 307, 466-471
16. Mutskov, V. J., Farrell, C. M., Wade, P. A., Wolffe, A. P., and Felsenfeld, G. (2002) *Genes Dev.* 16, 1540-1554
17. Yusufzai, T. M. and Felsenfeld, G. (2004) *Proc. Natl. Acad. Sci. U.S.A* 101, 8620-8624
18. Bell, A. C., West, A. G., and Felsenfeld, G. (1999) *Cell* 98, 387-396
19. Chung, J. H., Bell, A. C., and Felsenfeld, G. (1997) *Proc. Natl. Acad. Sci. U.S.A* 94, 575-580
20. Chung, J. H., Whiteley, M., and Felsenfeld, G. (1993) *Cell* 74, 505-514
21. Lanigan, T. M. and Russo, A. F. (1997) *J. Biol. Chem.* 272, 18316-18324
22. Symes, A. J., Craig, R. K., and Brickell, P. M. (1992) *FEBS Lett.* 306, 229-233
23. Wada, C., Hashimoto, C., Kameya, T., Yamaguchi, K., and Ono, M. (1988) *Virchows Arch. B Cell Pathol. Incl. Mol. Pathol.* 55, 217-223
24. Viney, T. J., Schmidt, T. W., Gierasch, W., Sattar, A. W., Yaggie, R. E., Kuburas, A., Quinn, J. P., Coulson, J. M., and Russo, A. F. (2004) *J. Biol. Chem.* 279, 49948-49955
25. Tverberg, L. A. and Russo, A. F. (1993) *J. Biol. Chem.* 268, 15965-15973
26. Yamamoto, M., Davydova, J., Takayama, K., Alemany, R., and Curiel, D. T. (2003) *J. Virol.* 77, 1633-1637
27. Hanawa, H., Yamamoto, M., Zhao, H., Shimada, T., and Persons, D. A. (2009) *Mol. Ther.* 17, 667-674
28. Guglielmi, L., Le, B. M., Truffinet, V., Cogne, M., and Denizot, Y. (2003) *Biochem. Biophys. Res. Commun.* 307, 466-471
29. Mutskov, V. J., Farrell, C. M., Wade, P. A., Wolffe, A. P., and Felsenfeld, G. (2002) *Genes Dev.* 16, 1540-1554
30. Yusufzai, T. M. and Felsenfeld, G. (2004) *Proc. Natl. Acad. Sci. U.S.A* 101, 8620-8624
31. Bell, A. C., West, A. G., and Felsenfeld, G. (1999) *Cell* 98, 387-396
32. Chung, J. H., Bell, A. C., and Felsenfeld, G. (1997) *Proc. Natl. Acad. Sci. U.S.A* 94, 575-580
33. Kuruppu, D., Dorfman, J. D., and Tanabe, K. K. (2007) *Curr. Cancer Drug Targets.* 7, 175-180

The complete disclosures of all references cited in this specification are hereby incorporated by reference. Also incorporated by reference is the complete disclosure of the priority application, U.S. provisional application No. 61/259,311 filed on Nov. 9, 2009. In the event of an otherwise irreconcilable conflict, however, the present specification shall control.

What is claimed:

1. A viral expression vector whose genome comprises: (a) the human INSM1 promoter; (b) a pair of tandem nicotinic acetylcholine receptor neuronal restrictive silencer elements downstream from said promoter; (c) an insulator element upstream from said promoter; and (d) one or more DNA sequences encoding a polypeptide toxin, or encoding a polypeptide reporter molecule, or encoding both a polypeptide toxin and a polypeptide reporter molecule;
   wherein:
   (i) said viral expression vector is competent to infect at least some mammalian cells;
   (ii) said insulator is adapted to block the influence of viral regulatory elements on the transcription within mammalian cells of said one or more DNA sequences, but not to affect the influence of said promoter or the influence of said neuronal restrictive silencer elements on the transcription of said one or more DNA sequences;
   (iii) said promoter is operatively linked to said one or more DNA sequences, and is adapted to cause the selective transcription of said one or more DNA sequences in tumor cells of neuroendocrine origin;
   (iv) said tandem neuronal restrictive silencer elements are operatively linked to said promoter, and are adapted to selectively repress the transcription of said one or more DNA sequences in non-neuronal cells;
   (v) the reporter molecule, if expressed, facilitates the identification of cells in which the reporter molecule is expressed; and the toxin, if expressed, is lethal or conditionally lethal to cells in which the toxin is expressed;
   whereby:
   said viral expression vector is adapted to be administered to a mammal in vivo, and to cause the selective in vivo expression of said one or more DNA sequences in tumor cells of neuroendocrine origin, without expression of said one or more DNA sequences in non-neuronal cells; whereby the reporter molecule, if expressed, facilitates the identification of tumor cells of neuroendocrine origin; and whereby the toxin, if expressed, is lethal or conditionally lethal to tumor cells of neuroendocrine origin.

2. The viral expression vector of claim 1, wherein said INSM1 promoter comprises all or a functional portion of base pairs −1661 to +40.

3. The viral expression vector of claim 1, wherein said insulator comprises the chicken HS4 β-globin insulator element.

4. The viral expression vector of claim 1, wherein said one or more DNA sequences encode the conditionally lethal toxin herpes simplex virus thymidine kinase.

5. The viral expression vector of claim 1, wherein said one or more DNA sequences encode a luciferase reporter molecule.

6. The viral expression vector of claim 1, wherein said one or more DNA sequences encode a secreted reporter molecule.

7. The viral expression vector of claim 1, wherein said viral expression vector is a non-replicating Ad5 adenoviral vector.

8. A method for detecting or diagnosing a neuroendocrine tumor in a mammalian patient, said method comprising administering to the patient the viral expression vector of claim 1, wherein said one or more DNA sequences encode a reporter molecule, and observing subsequent expression of the encoded reporter molecule in the patient's tissues as a measure of the presence or the extent of a neuroendocrine tumor.

9. The method of claim 8, wherein the neuroendocrine tumor is selected from the group consisting of medulloblastoma, neuroblastoma, small cell lung carcinoma, non-small cell carcinoma with neuroendocrine phenotype, carcinoid, insulinoma, pheochromocytoma, medullary thyroid carcinoma, pituitary tumors, prostate carcinomas, and retinoblastoma tumors.

10. A method for treating a neuroendocrine tumor in a mammalian patient, said method comprising administering to the patient the viral expression vector of claim 1, wherein said one or more DNA sequences encode a toxin, and selectively expressing the encoded toxin within cells of the neuroendocrine tumor; and wherein, if said toxin is only conditionally lethal, then said method additionally comprises the step of providing conditions that produce the lethal phenotype; whereby cells of the neuroendocrine tumor are selectively killed.

11. The method of claim 10, wherein the neuroendocrine tumor is selected from the group consisting of medulloblastoma, neuroblastoma, small cell lung carcinoma, non-small cell carcinoma with neuroendocrine phenotype, carcinoid, insulinoma, pheochromocytoma, medullary thyroid carcinoma, pituitary tumors, prostate carcinoma, and retinoblastoma tumors.

12. A method for detecting or diagnosing a neuroendocrine tumor in a mammalian patient, said method comprising treating a biopsy specimen from the patient with the viral expression vector of claim 1, wherein said one or more DNA sequences encode a reporter molecule, and observing subsequent expression of the encoded reporter molecule in the specimen in vitro as a measure of the presence or the extent of a neuroendocrine tumor.

* * * * *